United States Patent
Pouchoulin

(10) Patent No.: US 10,625,014 B2
(45) Date of Patent: Apr. 21, 2020

(54) APPARATUS FOR EXTRACORPOREAL TREATMENT OF BLOOD AND METHOD OF CONTROL OF A BLOOD-WARMING DEVICE IN AN EXTRACORPOREAL BLOOD TREATMENT APPARATUS

(71) Applicant: GAMBRO LUNDIA AB, Lund (SE)

(72) Inventor: Dominique Pouchoulin, Tramoyes (FR)

(73) Assignee: GAMBRO LUNDIA AB, Lund (SE)

( * ) Notice: Subject to any disclaimer, the term of this patent is extended or adjusted under 35 U.S.C. 154(b) by 469 days.

(21) Appl. No.: 15/021,226

(22) PCT Filed: Sep. 4, 2014

(86) PCT No.: PCT/EP2014/068867
§ 371 (c)(1),
(2) Date: Mar. 10, 2016

(87) PCT Pub. No.: WO2015/036316
PCT Pub. Date: Mar. 19, 2015

(65) Prior Publication Data
US 2016/0220748 A1     Aug. 4, 2016

(30) Foreign Application Priority Data

Sep. 12, 2013   (EP) .................................. 13184067

(51) Int. Cl.
*A61M 1/36* (2006.01)
*A61M 1/16* (2006.01)

(52) U.S. Cl.
CPC .......... *A61M 1/369* (2013.01); *A61M 1/1601* (2014.02); *A61M 1/3621* (2013.01); *A61M 1/3663* (2013.01); *A61M 2205/3334* (2013.01); *A61M 2205/3368* (2013.01); *A61M 2205/35* (2013.01); *A61M 2205/36* (2013.01)

(58) Field of Classification Search
None
See application file for complete search history.

(56) References Cited

U.S. PATENT DOCUMENTS

2006/0241543 A1* 10/2006 Gura ....................... A61M 1/16
                                                         604/5.01
2009/0099498 A1    4/2009 Demers et al.

FOREIGN PATENT DOCUMENTS

WO       03/055543        7/2003

OTHER PUBLICATIONS

European Search Report—EP13184067.0-1651 dated Dec. 6, 2013, 10 pages.

(Continued)

*Primary Examiner* — Richard C Gurtowski
(74) *Attorney, Agent, or Firm* — K&L Gates LLP

(57) ABSTRACT

An extracorporeal blood treatment apparatus (1) comprising a control unit (10) connectable to a blood warming device (200) and configured to issue a control signal for the blood warming device, wherein the control signal comprises a command directed to impose to the blood warming device (200) a modality of operation depending upon an identified mode of current operation of the blood treatment apparatus. A method for controlling the blood treatment apparatus (1) and an assembly including the blood treatment apparatus (1) and the blood warming device (200) are also disclosed.

29 Claims, 7 Drawing Sheets

(56) References Cited

OTHER PUBLICATIONS

International Search Report—PCT/EP2014/068867 dated Nov. 3, 2014, 6 pages.
Written Opinion of the International Searching Authority—PCT/EP2014/068867 dated Nov. 3, 2014, 12 pages.

* cited by examiner

APPARATUS FOR EXTRACORPOREAL TREATMENT OF BLOOD AND METHOD OF CONTROL OF A BLOOD-WARMING DEVICE IN AN EXTRACORPOREAL BLOOD TREATMENT APPARATUS

PRIORITY CLAIM

The present application is a National Phase of International Application No. PCT/EP2014/068867, filed on Sep. 4, 2014, which claims priority to European Patent Application No. 13184067.0, filed Sep. 12, 2013, the entire contents of each of which are incorporated herein by reference and relied upon.

The present invention relates to an apparatus for extracorporeal treatment of blood. In accordance with certain aspects, the extracorporeal treatment apparatus according to the invention is coupled to, or comprises, a blood-warming device. The invention also concerns a method of control of a blood-warming device wherein the blood-warming device may be part of the extracorporeal blood treatment apparatus or may be a separate device, which is in communication with an extracorporeal blood treatment apparatus.

Extracorporeal blood treatment involves removing blood from a patient, treating the blood externally to the patient, and returning the treated blood to the patient. Extracorporeal blood treatment is typically used to extract undesirable matter or molecules from the patient's blood and add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, for example.

Extracorporeal blood treatment is typically accomplished by removing the blood from the patient in e.g. a continuous flow, introducing the blood into a primary chamber, also referred to as blood chamber, of a treatment unit (such as a dialyzer or an hemofilter) where the blood is allowed to flow past a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment.

A number of different types of extracorporeal blood treatments may be performed. In an ultrafiltration (UF) treatment, undesirable matter is removed from the blood by convection across the membrane into the secondary chamber. In a hemofiltration (HF) treatment, the blood flows past the semipermeable membrane as in UF and desirable matter is added to the blood, typically by dispensing a fluid into the blood either before and/or after it passes through the treatment unit and before it is returned to the patient. In a hemodialysis (HD) treatment, a secondary fluid containing desirable matter is introduced into the secondary chamber of the treatment unit. Undesirable matter from the blood crosses the semipermeable membrane into the secondary fluid and desirable matter from the secondary fluid may cross the membrane into the blood. In a hemodiafiltration (HDF) treatment, blood and secondary fluid exchange matter as in HD, and, in addition, matter is added to the blood, typically by dispensing a fluid into the treated blood before its return to the patient as in HF.

During extracorporeal blood treatment therapies, the patient may lose significant amount of heat due to fluid exchange by diffusion or convection, and due to heat lost to the atmosphere. As extracorporeal blood treatments may last from several hours up to several days, the patient is put at risk of hypothermia in case no preventive measures are taken. This risk is, for example, present both in the case of relatively short treatments with high volume exchange, like chronic HD, and in the case of low volume but continuous therapies like continuous renal replacement therapy (CRRT). Furthermore, the risk of hypothermia is even more problematic in case of treatments applied to low body weight patients, such as children.

In order to prevent hypothermia during extracorporeal blood treatment several solutions have been developed in the past.

In accordance with a first known solution described in U.S. Pat. No. 4,894,164, the dialysis fluid used for dialyzing blood is warmed-up in order to try to balance the heat lost by the blood circulating in the extracorporeal blood circuit. This solution presents however a number of drawbacks. Warming of dialysate or replacement fluids requires managing fluid degassing, and may lead to precipitation problems when using bicarbonate solutions. Moreover, warming of treatment fluid does not offer a response to patients' cooling during therapies where there is no use of dialysis and/or infusion fluid, such as in hemoperfusion therapies or in ultrafiltration therapies. Additionally, fluid warming requires multiplying the heating and degassing means on each fluid circuit.

In accordance with a second known solution, and in order to solve the above problems, blood warmers acting on the bloodline, and capable of directly warming blood, have been used. Blood warmers directly acting on the extracorporeal blood circuit have several benefits with respect to warming the dialysis or the infusion fluid: in fact, blood warmers may be used with all type of therapies and do not cause problems of precipitation of solutes. Furthermore, as blood warmers act directly on the extracorporeal blood circuit it may be easier to control blood temperature. It should be noted that the blood warmers currently on the marketplace are formed by a device distinct from the extracorporeal blood treatment apparatus and operating independently from this latter. Although these blood-warming units are designed for being safe when operating on their own in the extracorporeal blood circuit, it is the purpose of the invention to further increase the safety of the blood-warming step.

It is an object of the present invention to render available an extracorporeal blood treatment apparatus capable of efficiently cooperating with a blood-warming device and providing increased safety during the blood-warming step.

It is a further object of the invention to provide an assembly including an extracorporeal blood treatment apparatus and a blood-warming device operating with increased safety.

Finally, it is a further object of the invention to provide a method of control capable of increasing the safety in the operation of blood warming devices.

SUMMARY

At least one of the above objects is substantially reached by an apparatus or by an assembly according to one or more of the appended claims.

At least one of the above objects is substantially reached by a method according to one or more of below described aspects.

An apparatus and assemblies for the extracorporeal treatment of blood according to aspects of the invention are here below described.

A $1^{st}$ aspect relates to an apparatus for extracorporeal treatment of blood comprising: a holding portion configured for receiving an extracorporeal blood circuit having a treatment unit, a blood withdrawal line connected to a blood inlet of the treatment unit, and a blood return line connected to an outlet of the treatment unit;

a blood pump which, when the extracorporeal blood circuit is received by the holding portion, is configured for controlling the flow of blood ($Q_{BLOOD}$) flowing through at least one of said blood withdrawal line and blood return line;

a control unit connectable, e.g. by means of a communication line, to a blood-warming device having heating components, the control unit being configured to execute the following control procedure:

establishing a communication with said blood-warming device, identifying, among a plurality of modes of operation of the apparatus, a current operational mode which the apparatus is performing, generating a control signal for the blood-warming device, the control signal comprising at least one of the following:

a command directed to impose to the blood-warming device a mode of operation depending upon the identified current operational mode of said apparatus;

an information defining said identified current operational mode.

In a $2^{nd}$ aspect according to the $1^{st}$ aspect, the control signal comprises both the following:

a command directed to impose to the blood-warming device a mode of operation depending upon the identified current operational mode of said apparatus;

an information defining said identified current operational mode.

In a $3^{rd}$ aspect according to any one of $1^{st}$ or $2^{nd}$ aspect, the communication is wired or wireless and in particular may be a wired bidirectional communication, or a wireless bidirectional communication, or a wired unidirectional communication (from the control unit to the control system only), or a wireless unidirectional communication (from the control unit to the control system only).

In a $4^{th}$ aspect according to any one of $1^{st}$ or $2^{nd}$ or $3^{rd}$ aspect, the step of identifying a mode of current operation of the apparatus comprises checking whether or not the mode of current operation is a mode wherein there is no blood flow through the extracorporeal blood circuit.

Examples of no blood flow modes can be: blood pump stop imposed by the operator, or end of treatment, or alarm conditions issued by the machine automatically halting the blood pump, etcetera.

In a $5^{th}$ aspect according to any one of the preceding aspects, the step of identifying a current operational mode of the apparatus comprises checking whether or not the current operational mode is a mode wherein the extracorporeal blood circuit is connected to a patient cardiovascular system.

Examples where the mode of operation is a mode wherein the extracorporeal blood circuit may not be connected to the patient are: priming of the extracorporeal blood circuit, priming of the fluid lines (other than blood line), disinfection of the apparatus.

In a $6^{th}$ aspect according to any one of the preceding aspects, the step of generating a control signal in said control procedure comprises the following:

if the identified current operational mode of the apparatus is a mode where there is no blood flow through the extracorporeal blood circuit or a mode wherein the extracorporeal blood circuit is not connected to a patient cardiovascular system, then configuring said command to impose a switch off of electric power at least to the heating components of the blood-warming device.

In a $7^{th}$ aspect according to any one of the preceding aspects, the control procedure further comprises receiving at least a power information signal including information related to the electric power P supplied to the heating components of said blood-warming device.

In a $8^{th}$ aspect according to any one of the preceding aspects, the step of generating a control signal in said control procedure comprises the following:

if the identified current operational mode of the apparatus is a mode where there is no blood flow through the extracorporeal blood circuit or a mode wherein the extracorporeal blood circuit is not connected to a patient cardiovascular system, then configuring said command to impose that the electric power supplied to the heating components of the blood warming apparatus be set to zero.

In a $9^{th}$ aspect according to any one of the preceding aspects from $1^{st}$ to $7^{th}$, the step of generating a control signal in said control procedure comprises the following:

if the identified current operational mode of the apparatus is a mode wherein there is no blood flow through the extracorporeal blood circuit or a mode wherein the extracorporeal blood circuit is not connected to a patient cardiovascular system, then imposing that the electric power supplied to the heating components of the blood warming apparatus be set to a minimum, different from zero.

In a $10^{th}$ aspect according to any one of the preceding aspects if the identified current operational mode is a mode wherein there is presence of blood flow in the extracorporeal blood circuit, the control procedure comprises repeating at least the identification step, after a certain time delay from a preceding identification step. The time delay may be a prefixed time delay, e.g., lasting from 1 to 30 minutes.

In a $11^{th}$ aspect according to any one of the preceding aspects if the identified current operational mode is a mode wherein there is presence of blood flow in the extracorporeal blood circuit, the control procedure comprises repeating at least the identification step, after detection of a change in the operating mode of said apparatus.

In a $12^{th}$ aspect according to any one of the preceding aspects, said apparatus comprises at least one treatment fluid line directly or indirectly connectable to said extracorporeal blood circuit and wherein the control procedure comprises calculating an electric power maximum threshold $P_{max}$ allowed to be supplied to the heating components of the blood warming apparatus, wherein the maximum threshold $P_{max}$ is calculated at least based on measured or set flow rates of fluid in said at least one treatment fluid line.

In a $13^{th}$ aspect according to the preceding aspect, the step of generating a control signal in said control procedure comprises the following:

if the identified current operational mode is a mode wherein there is presence of blood flow in the extracorporeal blood circuit, the control unit includes in the control signal a further command which is directed to impose that the electric power P supplied to the heating components of the blood-warming device be below said maximum threshold $P_{max}$.

In a 14th aspect according to any one of the preceding two aspects, the apparatus has the extracorporeal blood circuit mounted on the holding portion, with the treatment unit having a semipermeable membrane dividing the same treatment unit into a blood chamber and a dialysate chamber, and wherein said at least one treatment fluid line of the apparatus comprises one or more in the group of:
- a fresh dialysate line connected to a dialysate inlet of said dialysate chamber,
- a pre-infusion line connected to said blood withdrawal line downstream said blood pump,
- a post-infusion line connected to said blood return line, optionally downstream said blood warmer,
- a pre-blood pump infusion line connected to said blood withdrawal line upstream said blood pump,
- a waste line connected to an outlet of said dialysate chamber.

In a 15th aspect according to any one of the preceding three aspects, wherein the maximum threshold $P_{max}$ is calculated at least based on one or more of the following flow rates:
- a dialysate flow rate $Q_{DIAL}$ which is a set or measured value of flow through said fresh dialysate line,
- a pre-infusion flow rate $Q_{REP1}$ which is a set or measured value of flow through said pre-infusion line,
- a post-infusion flow rate $Q_{REP2}$ which is a set or measured value of flow through said post-infusion line,
- a pre-blood pump infusion flow rate $Q_{PBP}$, which is a set or measured value of flow through said pre-blood pump infusion line,
- an effluent flow rate $Q_{EFF}$ which is a set or measured flow rate through the effluent line.

In a 16th aspect according to the preceding aspect, wherein the maximum threshold $P_{max}$ is calculated at least based on:
- a dialysate flow rate $Q_{DIAL}$ which is a set or measured value of flow through said fresh dialysate line.

In a 17th aspect according to any one of the preceding two aspects, wherein the maximum threshold $P_{max}$ is calculated at least based on:
- a pre-infusion flow rate $Q_{REP1}$ which is a set or measured value of flow through said pre-infusion line.

In a 18th aspect according to any one of the preceding three aspects, wherein the maximum threshold $P_{max}$ is calculated at least based on:
- a post-infusion flow rate $Q_{REP2}$ which is a set or measured value of flow through said post-infusion line.

In a 19th aspect according to any one of the preceding four aspects wherein the maximum threshold $P_{max}$ is calculated at least based on:
- a pre-blood pump infusion flow rate $Q_{PBP}$, which is a set or measured value of flow through said pre-blood pump infusion line.

In a 20th aspect according to any one of the preceding five aspects wherein the maximum threshold $P_{max}$ is calculated at least based on:
- an effluent flow rate $Q_{EFF}$ which is a set or measured flow rate through the effluent line.

In a 21st aspect it is provided an extracorporeal blood treatment apparatus comprising:
- a holding portion configured for receiving an extracorporeal blood circuit having a treatment unit, a blood withdrawal line connected to a blood inlet of the treatment unit, and a blood return line connected to an outlet of the treatment unit;
- a blood pump which, when the extracorporeal blood circuit is received by the holding portion, is configured for controlling the flow of blood ($Q_{BLOOD}$) flowing through at least one of said blood withdrawal line and blood return line;
- a control unit configured for communicating to a blood-warming device, the control unit being configured to execute the following control procedure:
    - calculating an electric power maximum threshold $P_{max}$ at least based on the flow rate through one or more of the following lines:
        - a fresh dialysate line connectable to the dialysate chamber of the treatment unit,
        - pre-infusion line connectable to the blood withdrawal line,
        - post infusion line connectable to the blood return line,
        - a pre-blood pump infusion line, and a
        - waste line connectable to an outlet of the dialysate chamber of said treatment unit.
    - generating and transmitting to the blood-warming device a control signal comprising at least one of the following:
        - a command directed to impose blood-warming device said maximum threshold $P_{max}$ as maximum electric power allowed to be supplied to the heating components of the blood warming device;
        - the calculated value of said maximum threshold $P_{max}$.

In a 22nd aspect it is provided an extracorporeal blood treatment apparatus comprising:
- a holding portion configured for receiving an extracorporeal blood circuit having a treatment unit, a blood withdrawal line connected to a blood inlet of the treatment unit, and a blood return line connected to an outlet of the treatment unit;
- a blood pump which, when the extracorporeal blood circuit is received by the holding portion, is configured for controlling the flow of blood ($Q_{BLOOD}$) flowing through at least one of said blood withdrawal line and blood return line;
- a control unit configured for communicating to a blood-warming device, the control unit being configured to execute the following control procedure:
    - calculating an electric power maximum threshold $P_{max}$ at least based on the flow rate through one or more of the following lines:
        - a fresh dialysate line connectable to the dialysate chamber of the treatment unit,
        - pre-infusion line connectable to the blood withdrawal line,
        - post infusion line connectable to the blood return line,
        - a pre-blood pump infusion line, and a
        - waste line connectable to an outlet of the dialysate chamber of said treatment unit.
    - generating and transmitting to the blood-warming device a control signal comprising both of the following:
        - a command directed to impose blood-warming device said maximum threshold $P_{max}$ as maximum electric power allowed to be supplied to the heating components of the blood warming device;
        - the calculated value of said maximum threshold $P_{max}$.

In a 23rd aspect according to any one of the preceding aspects, the control procedure further includes:
- receiving from the blood-warming device at least a power information signal indicative of the electric power P currently supplied to the heating components of the blood-warming device,
- comparing said supplied electric power P against said/a maximum threshold $P_{max}$, and if it is detected that the supplied electric power P is greater or equal to said maximum threshold $P_{max}$, configure said command included in the control signal to reduce the electrical power P supplied to the heating components of the blood-warming device.

In a 24$^{th}$ aspect according to any one of the preceding aspects, the control procedure further includes:
receiving from the blood-warming device at least a power information signal indicative of the electric power P currently supplied to the heating components of the blood-warming device,
comparing said supplied electric power P against said/a maximum threshold $P_{max}$, and if it is detected that the supplied electric power P is greater or equal to said maximum threshold $P_{max}$, configure said to command included in the control signal to reduce to zero the electrical power P supplied to the heating components of the blood-warming device.

In a 25$^{th}$ aspect according to any one of the preceding aspects, the control procedure further includes:
receiving from the blood-warming device at least a power information signal indicative of the electric power P currently supplied to the heating components of the blood-warming device,
comparing said supplied electric power P against said/a maximum threshold $P_{max}$, and if it is detected that the supplied electric power P is greater or equal to said maximum threshold $P_{max}$, configure said command included in the control signal to switch off the blood-warming device.

In a 26$^{th}$ aspect according to any one of the preceding aspects, the/a maximum threshold $P_{max}$ is calculated at least based on the non zero fluid flow rates injected in blood and exchanged in the blood treatment unit.

In a 27$^{th}$ aspect according to any one of the preceding aspects, the/a maximum threshold $P_{max}$ is calculated at least based on the non zero fluid flow rates and on the respective temperatures of the fluids exchanged by the apparatus during the treatment through one or more of said fresh dialysate line, pre-infusion line, post infusion line, pre-blood pump infusion line, and waste line.

In a 28$^{th}$ aspect according to any one of the preceding aspects, the/a maximum threshold $P_{max}$ is calculated at least based on the fluid flow rate and on the respective temperature of the fluid exchanged by the apparatus during the treatment through said fresh dialysate line.

In a 29$^{th}$ aspect according to any one of the preceding aspects, the/a maximum threshold $P_{max}$ is calculated at least based on the fluid flow rate and on the respective temperature of the fluid exchanged by the apparatus during the treatment through said pre-infusion line.

In a 30$^{th}$ aspect according to any one of the preceding aspects, the/a maximum threshold $P_{max}$ is calculated at least based on the fluid flow rate and on the respective temperature of the fluid exchanged by the apparatus during the treatment through said post infusion line.

In a 31$^{st}$ aspect according to any one of the preceding aspects, the/a maximum threshold $P_{max}$ is calculated at least based on the fluid flow rate and on the respective temperature of the fluid exchanged by the apparatus during the treatment through said pre-blood pump infusion line.

In a 32$^{nd}$ aspect according to any one of the preceding aspects, the/a maximum threshold $P_{max}$ is calculated at least based on the fluid flow rate and on the respective temperature of the fluid exchanged by the apparatus during the treatment through said waste line.

In a 33$^{rd}$ aspect according to any one of the preceding aspects, the/a maximum threshold $P_{max}$ is calculated at least based on said measured or set flow of blood $Q_{BLOOD}$.

In a 34$^{th}$ aspect according to any one of the preceding aspects, the/a maximum threshold $P_{max}$ is calculated based also on a room temperature value, which is the value of temperature in the room where the treatment is taking place with the apparatus, said room temperature value being a measured value or a set value entered by the user or a preset value stored in the control unit.

In a 35$^{th}$ aspect according to any one of the preceding aspects the control procedure comprises receiving a set value for the temperature desired in the blood returning to patient and calculating said/a maximum threshold $P_{max}$ also based on said desired blood temperature value.

In a 36$^{th}$ aspect according to any one of the preceding aspects the/a maximum threshold $P_{max}$ is calculated at least based on:
a desired blood temperature value, namely the blood temperature at which it is desired to bring blood returning to patient,
the fluid temperature values of the fluid fed to the fresh dialysate line, pre-infusion line, post-infusion line, pre-blood pump infusion line, and any other line connected to the blood circuit,
each of the values of the non zero fluid flow rates injected into the extracorporeal blood circuit or exchanged with the blood treatment unit which, depending upon the configuration of the apparatus include one or more of:
dialysate flow rate $Q_{DIAL}$, pre-infusion flow rate $Q_{REP1}$, post-infusion flow rate $Q_{REP2}$, a pre-blood pump infusion flow rate $Q_{PBP}$, the flow rate of any other line connected to the extracorporeal blood circuit.

In a 37$^{th}$ aspect according to any one of the preceding aspects the/a maximum threshold $P_{max}$ is calculated also based on a warmer efficiency coefficient q relating electrical consumption of the heating elements to the heat power transferred to the blood.

A 38$^{th}$ aspect concerns an assembly including an extracorporeal blood treatment apparatus according to any one of the preceding aspects and a blood-warming device, wherein the blood-warming device has a heating section provided with the heating components and configured for receiving and heating a corresponding portion of the extracorporeal blood circuit.

In a 39$^{th}$ aspect according to the preceding aspect the blood-warming device and the extracorporeal blood treatment apparatus are distinct, the blood-warming device comprising:
a respective power supply unit or system distinct from that of the apparatus,
a respective control system distinct from the apparatus control unit.

In a 40$^{th}$ aspect according to any one of the preceding two aspects, the extracorporeal blood treatment apparatus communication to the blood-warming device comprises a unidirectional communication between the control unit of the extracorporeal blood treatment apparatus and the control system of the blood-warming device.

In a 41$^{st}$ aspect according to any one of the preceding aspects38$^{th}$ or 39$^{th}$ wherein the extracorporeal blood treatment apparatus communication with the blood-warming device comprises a bidirectional communication between the control unit of the extracorporeal blood treatment apparatus and the control system of the blood-warming device.

In a 42$^{nd}$ aspect according to the 38$^{th}$ aspect the blood-warming device is a component part of the extracorporeal treatment apparatus and wherein the control unit of the apparatus includes the control system of the warming device and is configured to execute:

a first task comprising said control procedure, and
a second task comprising:
  receiving the control signal,
  executing said command.

In a 43$^{rd}$ aspect according to the any one of aspects from the 38$^{th}$ to the 41$^{st}$, the control system of the blood-warming device is configured to:
  receive the control signal,
  execute said command included in the control signal.

In a 44$^{th}$ aspect according to the any one of aspects from the 38$^{th}$ to the 41$^{st}$ or according to the 43$^{rd}$ aspect, the control system of the blood-warming device is configured to:
  receive said information defining said identified mode of current operation of the apparatus, and
  if the identified mode of current operation of the apparatus is a mode wherein there is no blood flow through the extracorporeal blood circuit or a mode wherein the extracorporeal blood circuit is not connected to a patient cardiovascular system, then impose a switch off or a reduction of electric power at least to the heating components of the blood-warming device.

In a 45$^{th}$ aspect according to the any one of aspects from the 38$^{th}$ to the 41$^{st}$ or according to the 43$^{rd}$ aspect or according to the 44$^{th}$ aspect, wherein the control system of the blood-warming device is configured to:
  receive said calculated value of the maximum threshold $P_{max}$,
  receive, from a power absorption sensor, a power information signal indicative of the electric power P currently supplied to the heating components of the blood-warming device,
  compare said supplied electric power P against said maximum threshold power $P_{max}$, and
  if it is detected that the supplied electric power P is greater or equal to said maximum threshold $P_{max}$, reduce the electrical power P supplied to the heating components, optionally setting said electric power P to zero.

A 46$^{th}$ aspect concerns a blood-warming device comprising:
  a heating section provided with heating components and configured for receiving and heating a corresponding portion of an extracorporeal blood circuit,
  a power supply unit or system connected to the heating components,
  a control system active on the power supply unit or system and connectable, e.g. by mans of a communication line, to the control unit of the apparatus according to any one of the preceding aspects from 1$^{st}$ to 37$^{th}$, wherein the control system is configured to:
    establish a communication with the control unit of said apparatus,
    receive the control signal,
    execute said command included in the control signal.

A 47$^{th}$ aspect concerns a blood-warming device comprising:
  a heating section provided with heating components and configured for receiving and heating a corresponding portion of an extracorporeal blood circuit,
  a power supply unit or system connected to the heating components,
  a control system active on the power supply unit or system and connectable, e.g. by means of a communication line, to the control unit of the apparatus according to any one of the preceding aspects from 1$^{st}$ to 37$^{th}$, wherein the control system is configured to:
    receive said information defining said current operational mode of the apparatus, and
    if the identified current operational mode of the apparatus is a mode wherein there is no blood flow through the extracorporeal blood circuit or a mode wherein the extracorporeal blood circuit is not connected to a patient cardiovascular system, then impose a switch off or a reduction of electric power at least to the heating components of the blood-warming device.

In a 48$^{th}$ aspect according to any one of the preceding two aspects the control system of the blood-warming device is configured to:
  receive said calculated value of the maximum threshold $P_{max}$,
  receive, from a power absorption sensor, a power information signal indicative of the electric power P currently supplied to the heating components of the blood-warming device,
  compare said supplied electric power P against said maximum threshold power Prnax, and
  if it is detected that the supplied electric power P is grater or equal to said maximum threshold $P_{max}$, reduce the electric power P supplied to the heating components.

In a 49$^{th}$ aspect according to the preceding aspect, if it is detected that the supplied electric power P is grater or equal to said maximum threshold $P_{max}$, the electric power P supplied to the heating components is set to zero.

A 50$^{th}$ concerns a method of controlling the electric power supplied to heating components of a blood-warming device active on an extracorporeal blood circuit of an extracorporeal blood treatment apparatus.

A 51$^{st}$ aspect concerns a method of controlling the electric power supplied to heating components of a blood-warming device active on an extracorporeal blood circuit of an extracorporeal blood treatment apparatus of the type according to any one of preceding aspects from 1$^{st}$ to 37$^{th}$.

In a 52$^{nd}$ aspect according to any one of the preceding two aspects, the method comprises execution of a control procedure (which may be executed by the control unit of the extracorporeal blood treatment apparatus of the apparatus according to any one of preceding aspects from 1$^{st}$ to 37$^{th}$) comprising the steps of:
  establishing a communication with said blood-warming device,
  identifying, among a plurality of modes of operation of the apparatus, a current operational mode which the apparatus is performing,
  generating a control signal for the blood-warming device, the control signal comprising at least one of the following:
    a command directed to impose to the blood-warming device a mode of operation depending upon the identified current operational mode of said apparatus;
    an information defining said identified current operational mode.

Note that the communication may be wired or wireless, and in particular it may be a wired bidirectional communication, or a wireless bidirectional communication, or a wired unidirectional communication (from the control unit to the control system only), or a wireless unidirectional communication (from the control unit to the control system only).

In a 53$^{rd}$ aspect according to the preceding aspect, the control signal comprises both the following:
  a command directed to impose to the blood-warming device a mode of operation depending upon the identified current operational mode of said apparatus;
  an information defining said identified current operational mode of the apparatus.

In a 54th aspect according to any one of 52nd or 53rd aspect, the step of identifying a mode of current operation of the apparatus comprises checking whether or not the mode of current operation is a mode of no blood flow through the extracorporeal blood circuit.

In a 55th aspect according to any one of the preceding 3 aspects, the step of identifying a current operational mode of the apparatus comprises checking whether or not the current operational mode is a mode wherein the extracorporeal blood circuit is connected to a patient cardiovascular system.

In a 56th aspect according to any one of the preceding 4 aspects, the step of generating a control signal in said control procedure comprises the following:

if the identified current operational mode of the apparatus is a mode where there is no blood flow through the extracorporeal blood circuit or a mode wherein the extracorporeal blood circuit is not connected to a patient cardiovascular system, then configuring said command to impose a switch off of electric power at least to the heating components of the blood-warming device.

In a 57th aspect according to any one of the preceding 5 aspects, the control procedure further comprises receiving at least a power information signal including information related to the electric power P supplied to the heating components of said blood-warming device.

In a 58th aspect according to any one of the 6 preceding aspects, the step of generating a control signal in said control procedure comprises the following:

if the identified current operational mode of the apparatus is a mode wherein there is no blood flow through the extracorporeal blood circuit or a mode wherein the extracorporeal blood circuit is not connected to a patient cardiovascular system, then configuring said command to impose that the electric power supplied to the heating components of the blood warming apparatus be set to zero.

In a 59th aspect according to any one of the preceding aspects from 52nd to 57th, the step of generating a control signal in said control procedure comprises the following:

if the identified current operational mode of the apparatus is a mode where there is no blood flow through the extracorporeal blood circuit or a mode wherein the extracorporeal blood circuit is not connected to a patient cardiovascular system, then imposing that the electric power supplied to the heating components of the blood warming apparatus be set to a minimum, different from zero.

In a 60th aspect according to any one of the preceding eight aspects if the identified current operational mode is a mode wherein there is presence of blood flow in the extracorporeal blood circuit, the control procedure comprises repeating at least the identification step, after a certain time delay from a preceding identification step. The time delay may be a prefixed time delay, e.g., lasting from 1 to 30 minutes.

In a 61st aspect according to any one of the preceding nine aspects if the identified current operational mode is a mode wherein there is presence of blood flow in the extracorporeal blood circuit, the control procedure comprises repeating at least the identification step, after detection of a change in the operating mode of said apparatus.

In a 62nd aspect according to any one of the preceding ten aspects, said apparatus comprises at least one treatment fluid line directly or indirectly connectable to said extracorporeal blood circuit and wherein the control procedure comprises calculating an electric power maximum threshold $P_{max}$ allowed to be supplied to the heating components of the blood warming apparatus, wherein the maximum threshold $P_{max}$ is calculated at least based on measured or set flow rates of fluid in said at least one treatment fluid line.

In a 63rd aspect according to the preceding aspect, the step of generating a control signal in said control procedure comprises the following:

if the identified current operational mode is a mode wherein there is presence of blood flow in the extracorporeal blood circuit, the control unit includes in the control signal a further command which is directed to impose that the electric power P supplied to the heating components of the blood-warming device be below said maximum threshold $P_{max}$.

In a 64th aspect according to any one of the preceding two aspects, the apparatus has the extracorporeal blood circuit mounted on the holding portion, with the treatment unit having a semipermeable membrane dividing the same treatment unit into a blood chamber and a dialysate chamber, and wherein said at least one treatment fluid line of the apparatus comprises one or more in the group of:

a fresh dialysate line connected to a dialysate inlet of said dialysate chamber, a pre-infusion line connected to said blood withdrawal line downstream said blood pump, a post-infusion line connected to said blood return line, optionally downstream said blood warmer, a pre-blood pump infusion line connected to said blood withdrawal line upstream said blood pump, a waste line connected to an outlet of said dialysate chamber.

In a 65th aspect according to any one of the preceding three aspects, wherein the maximum threshold $P_{max}$ is calculated at least based on one or more of the following flow rates:

a dialysate flow rate $Q_{DIAL}$ which is a set or measured value of flow through said fresh dialysate line, a pre-infusion flow rate $Q_{REP1}$ which is a set or measured value of flow through said pre-infusion line, a post-infusion flow rate $Q_{REP2}$ which is a set or measured value of flow through said post-infusion line, a pre-blood pump infusion flow rate $Q_{PBP}$, which is a set or measured value of flow through said pre-blood pump infusion line, an effluent flow rate $Q_{EFF}$ which is a set or measured flow rate through the effluent line.

In a 66th aspect according to the preceding aspect, wherein the maximum threshold $P_{max}$ is calculated at least based on:

a dialysate flow rate $Q_{DIAL}$ which is a set or measured value of flow through said fresh dialysate line.

In a 67th aspect according to any one of the preceding two aspects, wherein the maximum threshold $P_{max}$ is calculated at least based on:

a pre-infusion flow rate $Q_{REP1}$ which is a set or measured value of flow through said pre-infusion line.

In a 68th aspect according to any one of the preceding three aspects, wherein the maximum threshold $P_{max}$ is calculated at least based on:

a post-infusion flow rate $Q_{REP2}$ which is a set or measured value of flow through said post-infusion line.

In a 69th aspect according to any one of the preceding four aspects wherein the maximum threshold $P_{max}$ is calculated at least based on:

a pre-blood pump infusion flow rate $Q_{PBP}$, which is a set or measured value of flow through said pre-blood pump infusion line.

In a 70th aspect according to any one of the preceding five aspects wherein the maximum threshold $P_{max}$ is calculated at least based on:
an effluent flow rate $Q_{EFF}$ which is a set or measured flow rate through the effluent line.

In a 71st aspect according to any one of preceding aspect from 52nd to 70th the control procedure comprises:
calculating an electric power maximum threshold $P_{max}$ at least based on the set or measured flow rate through one or more of the following lines:
a fresh dialysate line connectable to the dialysate chamber of the treatment unit,
a pre-infusion line connectable to the blood withdrawal line,
a post infusion line connectable to the blood return line,
a pre-blood pump infusion line,
and a waste line connectable to an outlet of the dialysate chamber of said treatment unit.
generating and transmitting to the blood-warming device a control signal comprising at least one of the following:
a command directed to impose blood-warming device said maximum threshold $P_{max}$ as maximum electric power allowed to be supplied to the heating components of the blood warming device; the calculated value of said maximum threshold $P_{max}$.

In a 72nd aspect according to any one of preceding aspect from 52nd to 70th the control procedure comprises:
calculating an electric power maximum threshold $P_{max}$ at least based on the flow rate through one or more of the following lines:
a fresh dialysate line connectable to the dialysate chamber of the treatment unit,
a pre-infusion line connectable to the blood withdrawal line,
a post infusion line connectable to the blood return line,
a pre-blood pump infusion line, and
a waste line connectable to an outlet of the dialysate chamber of said treatment unit.
generating and transmitting to the blood-warming device a control signal comprising both of the following: a command directed to impose blood-warming device said maximum threshold $P_{max}$ as maximum electric power allowed to be supplied to the heating components of the blood warming device;
the calculated value of said maximum threshold $P_{max}$.

In a 73rd aspect according to any one of the preceding aspects from 52nd to 72nd, the control procedure further includes:
receiving from the blood-warming device at least a power information signal indicative of the electric power P currently supplied to the heating components of the blood-warming device,
comparing said supplied electric power P against said/a maximum threshold $P_{max}$, and if it is detected that the supplied electric power P is greater or equal to said maximum threshold $P_{max}$, configure said command included in the control signal to reduce the electrical power P supplied to the heating components of the blood-warming device.

In a 74th aspect according to any one of the preceding aspects from 52nd to 73rd, the control procedure further includes:
receiving from the blood-warming device at least a power information signal indicative of the electric power P currently supplied to the heating components of the blood-warming device,
comparing said supplied electric power P against said/a maximum threshold $P_{max}$, and if it is detected that the supplied electric power P is greater or equal to said maximum threshold $P_{max}$, configure said command included in the control signal to reduce to zero the electrical power P supplied to the heating components of the blood-warming device.

In a 75th aspect according to any one of the preceding aspects from 52nd to 74th, the control procedure further includes:
receiving from the blood-warming device at least a power information signal indicative of the electric power P currently supplied to the heating components of the blood-warming device,
comparing said supplied electric power P against said/a maximum threshold $P_{max}$, and if it is detected that the supplied electric power P is greater or equal to said maximum threshold $P_{max}$, configure said command included in the control signal to switch off the blood-warming device.

In a 76th aspect according to any one of the preceding aspects from 52nd to 75th, the/a maximum threshold $P_{max}$ is calculated at least based on the non zero fluid flow rates injected in blood and exchanged in the blood treatment unit.

In a 77th aspect according to any one of the preceding aspects from 52nd to 76th, the/a maximum threshold $P_{max}$ is calculated at least based on the non zero fluid flow rates and on the respective temperatures of the fluids exchanged by the apparatus during the treatment through one or more of said fresh dialysate line, pre-infusion line, post infusion line, pre-blood pump infusion line, and waste line.

In a 78th aspect according to any one of the preceding aspects from 52nd to 77th, the/a maximum threshold $P_{max}$ is calculated at least based on the fluid flow rate and on the respective temperature of the fluid exchanged by the apparatus during the treatment through said fresh dialysate line.

In a 79th aspect according to any one of the preceding aspects preceding aspects from 52nd to 78th, the/a maximum threshold $P_{max}$ is calculated at least based on the fluid flow rate and on the respective temperature of the fluid exchanged by the apparatus during the treatment through said pre-infusion line.

In a 80th aspect according to any one of the preceding aspects from 52nd to 79th, the/a maximum threshold $P_{max}$ is calculated at least based on the fluid flow rate and on the respective temperature of the fluid exchanged by the apparatus during the treatment through said post infusion line.

In a 81st aspect according to any one of the preceding aspects from 52nd to 80th, the a maximum threshold $P_{max}$ is calculated at least based on the fluid flow rate and on the respective temperature of the fluid exchanged by the apparatus during the treatment through said pre-blood pump infusion line.

In a 82nd aspect according to any one of the preceding aspects from 52nd to 81st, the/a maximum threshold $P_{max}$ is calculated at least based on the fluid flow rate and on the respective temperature of the fluid exchanged by the apparatus during the treatment through said waste line.

In a 83rd aspect according to any one of the preceding aspects from 52nd to 82nd, the/a maximum threshold $P_{max}$ is calculated at least based on said measured or set flow of blood $Q_{BLOOD}$.

In a 84th aspect according to any one of the preceding aspects from 52nd to 83rd, the/a maximum threshold $P_{max}$ is calculated based also on a room temperature value, which is the value of temperature in the room where the treatment is taking place with the apparatus, said room temperature value being a measured value or a set value entered by the user or a preset value stored in the control unit.

In a 85$^{th}$ aspect according to any one of the preceding aspects from 52$^{nd}$ to 84$^{th}$ the control procedure comprises receiving a set value for the temperature desired in the blood returning to patient and calculating said/a maximum threshold P$_{max}$ also based on said desired blood temperature value.

In a 86$^{th}$ aspect according to any one of the preceding aspects from 52$^{nd}$ to 85$^{th}$ the/a maximum threshold P$_{max}$ is calculated at least based on:
- a desired blood temperature value, namely the blood temperature at which it is desired to bring blood returning to patient,
- the fluid temperature values of the fluid fed to the fresh dialysate line, pre-infusion line, post-infusion line, pre-blood pump infusion line, and any other line connected to the blood circuit,
- each of the values of the non zero fluid flow rates injected into the extracorporeal blood circuit or exchanged with the blood treatment unit which, depending upon the configuration of the apparatus include one or more of: dialysate flow rate Q$_{DIAL}$, pre-infusion flow rate Q$_{REP1}$, post-infusion flow rate Q$_{REP2}$, a pre-blood pump infusion flow rate Q$_{PBP}$, the flow rate of any other line connected to the extracorporeal blood circuit.

In a 87$^{th}$ aspect according to any one of the preceding aspects from 52$^{nd}$ to 86$^{th}$ the/a maximum threshold P$_{max}$ is calculated also based on a warmer efficiency coefficient q relating electrical consumption of the heating elements to the heat power transferred to the blood.

In an 88$^{th}$ aspect according to any one of the preceding aspects wherein the fluid flown in said one or more treatment fluid lines is a liquid (e.g., an aqueous solution) or a gas (e.g. an oxygen containing gas).

In a 89$^{th}$ aspect a data carrier including instructions executable by a control unit of a blood treatment apparatus is provided. The instructions are configured such that, when executed by the control unit, they cause execution of the control procedure according to any one of the preceding aspects from 52$^{nd}$ to 87$^{th}$.

In a 90$^{th}$ aspect according to the preceding aspect the data carrier can be any support suitable for storing data, such as by way of non-limiting example: a RAM, a ROM, an EPROM, an optical or a magnetic disc, an electromagnetic wave, a mass memory storage device such as an Hard Disk or a flash memory bank.

In a 91$^{st}$ aspect according to any one of the preceding two aspects the extracorporeal blood treatment apparatus is of the type according to aspects from 1$^{st}$ to 37$^{th}$.

In a 92$^{nd}$ aspect according to any one of the preceding aspects the control procedure comprises the step of sending the control signal to the blood warming device. In particular the control unit of the extracorporeal blood treatment apparatus according to aspects from 1$^{st}$ to 37$^{th}$ may be configured to send the control signal to the control system of the blood treatment device.

DESCRIPTION OF THE DRAWINGS

Aspects of the invention are shown in the attached drawings, which are provided by way of non-limiting example, wherein.

DETAILED DESCRIPTION

Figure 1:
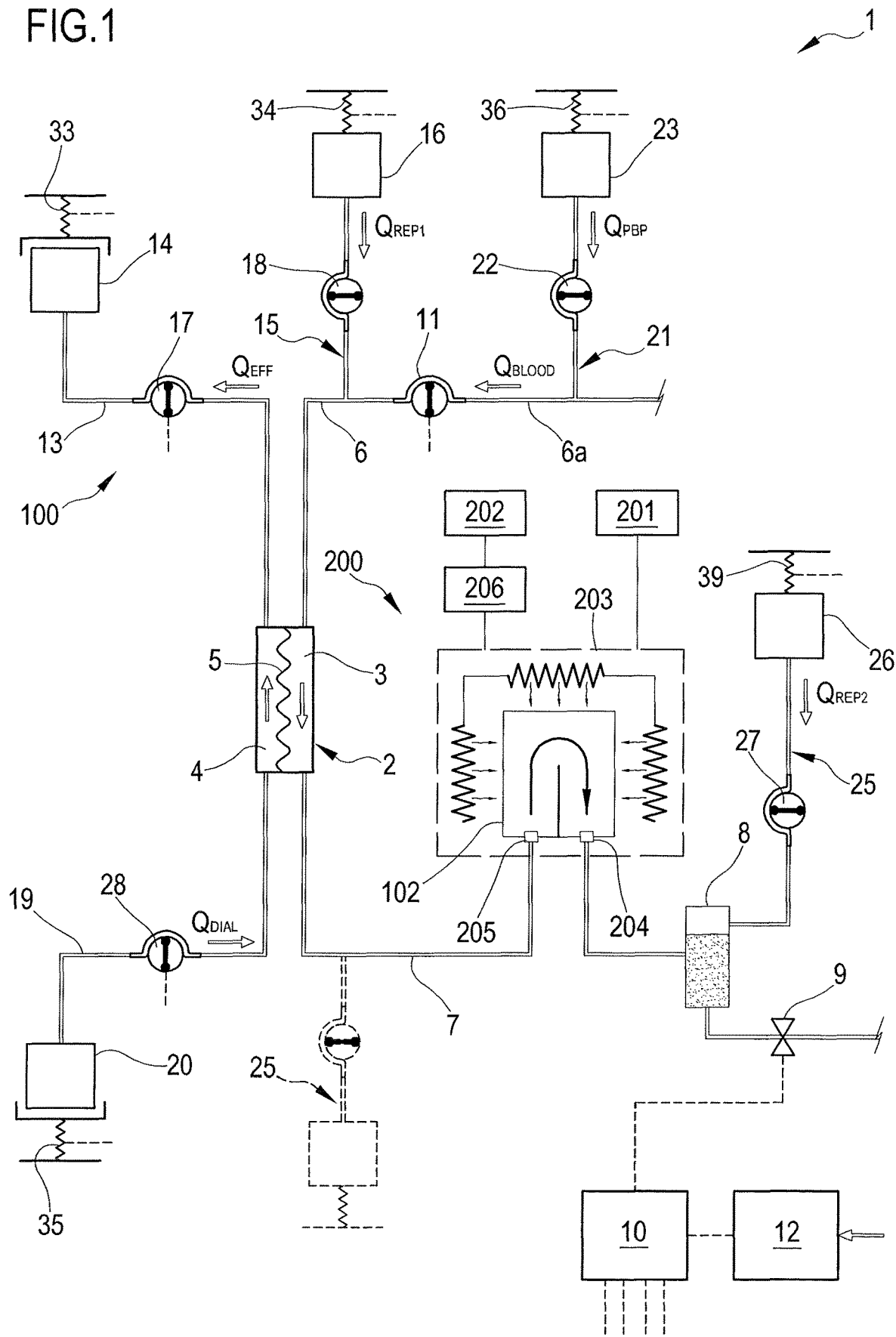
FIG. 1 schematically shows a first example of a blood treatment apparatus.
Figure 2:
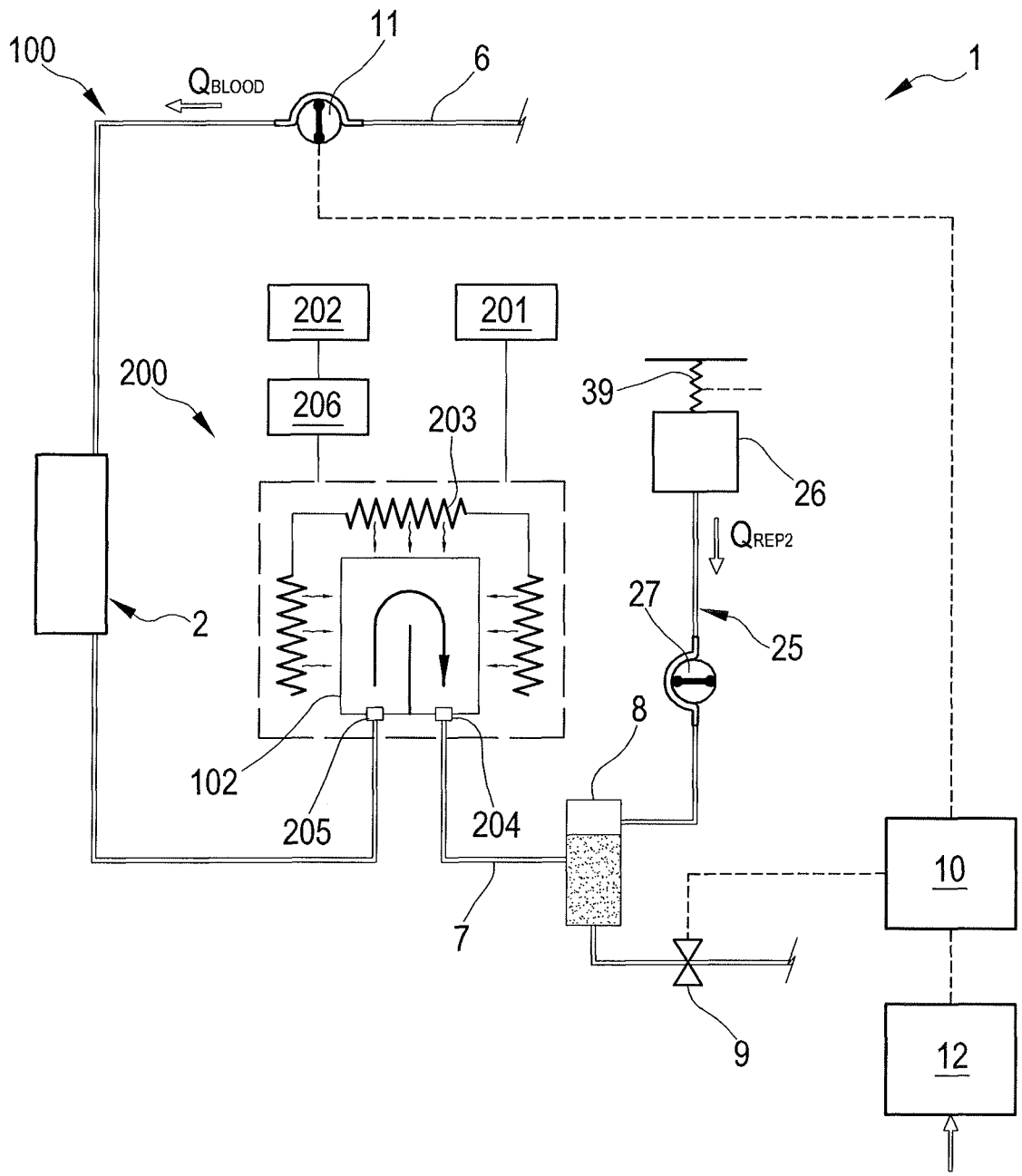
FIG. 2 schematically shows a second example of a blood treatment.

FIGS. 1 and 2 show exemplifying, and non limiting, embodiments of an apparatus for extracorporeal treatment of blood. Note that same components are identified by same reference numerals in FIGS. 1 and 2. FIG. 1 schematically shows a first example of a blood treatment apparatus 1 designed for delivering any one of the following treatments: hemodialysis, hemofiltration, hemodiafiltration, and ultrafiltration.

Figure 6:
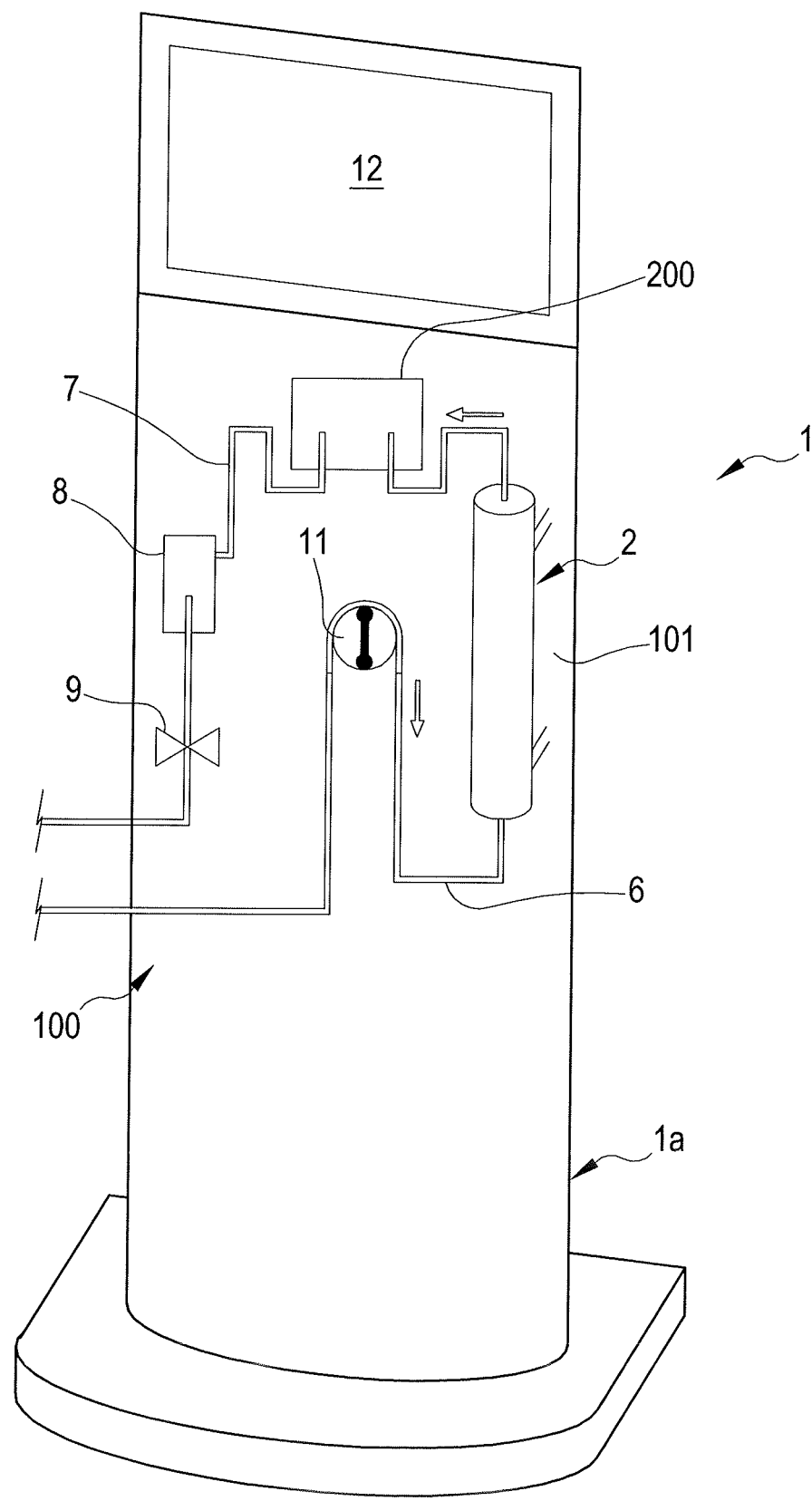
FIG. 6 shows a schematic elevation view of a cabinet of a blood treatment apparatus, e.g. of the type of FIG. 1 or FIG. 2, having a front panel configured for holding an extracorporeal blood circuit.

The apparatus 1 comprises a treatment unit 2 having a primary chamber 3 and a secondary chamber 4 separated by a semipermeable membrane 5. Depending upon the treatment, the membrane of the treatment unit may be selected to have different properties and performances. A blood withdrawal line 6 is connected to an inlet of the primary chamber 3, and a blood return line 7 is connected to an outlet of the primary chamber 3. The blood withdrawal line, the primary chamber 3 and the blood return line 7 are part of an extracorporeal blood circuit 100. In use, the extracorporeal blood circuit 100 is mounted on a holding portion 101 of the apparatus 1. Referring to FIG. 6, the holding portion 101 may be a front or a side panel of the cabinet 1a of the apparatus 1.

In use, the blood withdrawal line 6 and the blood return line 7 are connected to a needle or to a catheter or other access device (not shown) which is then placed in fluid communication with the patient vascular system, such that blood can be withdrawn through the blood withdrawal line, passed through the primary chamber and then returned to the patient's vascular system through the blood return line 7.

An air separator, such as a bubble trap 8 may be present on the blood return line 7. Moreover, a safety clamp 9 controlled by a control unit 10 may be present on the blood return line 7 downstream the bubble trap 8. A bubble sensor, for instance associated with the bubble trap 8 or coupled to a portion of the line 7 between the bubble trap 8 and the clamp 9 may be present. If present, the bubble sensor is connected to the control unit 10 and sends to the control unit 10 signals for the control unit to cause closure of the clamp 9 in case one or more bubbles above certain safety thresholds are detected.

As shown in FIG. 1, the blood flow Q$_{BLOOD}$ through the blood lines is controlled by a blood pump 11, for instance a peristaltic blood pump, acting either on the blood withdrawal line (as shown in FIG. 1) or on the blood return line. An operator may enter a set value for the blood flow rate $Q_{BLOOD}$ through a user interface 12, and the control unit 10, during treatment, may be configured to control the blood pump based on the set blood flow rate. The control unit 10 may comprise a digital processor (CPU) and memory (or memories), an analog circuit, or a combination thereof as explained in greater detail in section 'control unit'.

An effluent fluid line 13 is connected, at one end, to an outlet of the secondary chamber 4 and, at another end, to a waste, for instance comprising an effluent fluid container 14 collecting the fluid extracted from the secondary chamber or a drainage line. The embodiment of FIG. 1 also presents a pre-dilution fluid line 15 connected to the blood withdrawal line. This line 15 supplies replacement fluid from an infusion fluid source, such as container 16, connected at one end of the pre-dilution fluid line.

Note that alternatively or in addition to the pre-dilution fluid line the apparatus of FIG. 1 may include a post-dilution fluid line 25 which may be connected to the blood return line 7 either at the bubble trap 8 or upstream the bubble trap 8 (this option is shown with dashed lines in FIG. 1) or even downstream the bubble trap (e.g. downstream clamp 9). The post-infusion line 25 connects an infusion fluid source, such as a container 26, to the blood return line. As mentioned, the apparatus of FIG. 1 may include both a pre-dilution fluid line and a post infusion fluid line 15 and 25. In this case, each infusion fluid line may be connected to a respective infusion fluid container or the two infusion fluid lines may receive infusion fluid from a same source of infusion fluid such as a same infusion fluid container. Additionally, the apparatus 1 may present a further infusion line 21 connected, at one end, with a portion 6a of the blood withdrawal line 6 positioned upstream the blood pump 11 and, at its other end, with a further infusion fluid container 23, which for instance may contain a drug, or a regional anticoagulant such as a citrate solution, or a nutrient solution or other. This further infusion line is herein referred to as pre-blood pump infusion line 21. The apparatus of FIG. 1, may further include a dialysis fluid line 19 connected at one end with a dialysis fluid container 20 and at its other end with the inlet of the secondary chamber 4 of the treatment unit.

Although the exemplifying apparatus shown in FIG. 1 comprises all lines 13, 19, 15, 21 and 25, this should not be read in a limitative manner. In fact the apparatus 1 may be of the type having only one or more of the above described lines. For instance the apparatus 1 may include:
- only effluent line 13;
- only the effluent line 13 and the dialysate line 19;
- only the effluent line and the pre-dilution infusion line 15;
- only the effluent line and the post-dilution infusion line 25;
- the effluent line 13, and the pre-dilution and the post-dilution infusion lines 15 and 25;
- the effluent line 13, the pre-dilution and the post-dilution infusion lines 15 and 25, the pre-blood pump infusion line 21.

Depending upon the type of apparatus 1, and thus depending upon the number and type of lines present, corresponding pumps may be present or not. An effluent fluid pump 17 operates on the effluent fluid line 13 under the control of said control unit 10 to regulate the flow rate $Q_{EFF}$ across the effluent fluid line 13. If the apparatus has a pre-dilution line 15, then a pre-infusion pump 18 acts on pre-dilution infusion line 15 to regulate the flow rate $Q_{REP1}$ through the same pre-dilution infusion line. If the apparatus has a post-dilution line 25, then a post-infusion pump 27 acts on post-dilution infusion line 25 to regulate the flow rate $Q_{REP2}$ through the same post-dilution infusion line. Note that in case of two infusion lines (pre-dilution and post-dilution) each infusion line may cooperate with a respective infusion pump 18, 27.

In case the apparatus has line 19, a dialysis liquid pump 28 works on the dialysis liquid fluid line 19 under the control of said control unit 10, to supply fluid from the dialysis liquid container to the secondary chamber at a flow rate $Q_{DIAL}$. In case line 21 is present, a pump 22, also controlled by control unit 10, may act on a segment of the pre-blood pump infusion line 21 to regulate a pre-blood pump infusion rate $Q_{PBP}$. The dialysis liquid pump 28, the infusion fluid pump or pumps 18, 27 and the effluent fluid pump 17 and the pump 22 are operatively connected to the control unit 10 which controls the pumps. The pump control may be carried out by the control unit based on set values of desired flow rates through the above lines as entered by the user or as pre-stored in a memory connected to the control unit 10.

In case the sources of the fluids are containers, such as bags as shown in FIG. 1, then scales 33, 34, 35, 36, 39 may be used to provide weight signals to the control unit 10 and thus allow the control unit to determine, e.g. periodically, the actual flow rate through each line 13, 15, 19, 21, 25 and regulate the pumps speed accordingly. Note that flow rate through the above lines or at least the overall weigh loss rate may be determined using sensors different from scales. For instance, Coriolis mass flow sensors, mechanical flow sensors, electromagnetic flow sensors, volumetric flow sensors could be used in order to detect or allow detection by the control unit of the actual flow rate through each of the above lines. Moreover, instead of using fluid containers 16, 20, 23, 26 the replacement fluid and/or the dialysis fluid may be produced online by the apparatus 1 and then supplied to the extracorporeal blood circuit (in case of replacement fluid) and to the second chamber 4 of the treatment unit 2 (in case of dialysis fluid).

The control unit 10 is also connected to the user interface 12, for instance a graphic user interface, which receives operator's inputs and displays the apparatus outputs. For instance, the graphic user interface 12 may include a touch screen, a display screen and hard keys for entering user's inputs or a combination thereof.

A second embodiment of the apparatus 1 is shown in FIG. 2. The apparatus of FIG. 2 is an extracorporeal blood treatment apparatus comprising a treatment unit 2 (which can be a filtering unit or a blood-gas exchanger or adsorption column or any other type of device configured to apply a treatment to incoming blood). A blood withdrawal line 6 is connected to a blood inlet to the treatment unit 2, and a blood return line 7 is connected to a blood outlet from the treatment unit. As in the embodiment of FIG. 1, the blood withdrawal line 6 and the blood return line 7 are connected in use to a needle or to a catheter or other access device (not shown) which is then placed in fluid communication with the patient vascular system, such that blood can be withdrawn through the blood withdrawal line, flown through treatment unit and then returned to the patient's vascular system through the blood return line.

An air separator, such as a bubble trap 8 may be present on the blood return line; moreover, a safety clamp 9 controlled by control unit 10 may be present on the blood return line downstream the bubble trap 8. A bubble sensor, for instance associated with the bubble trap 8 or coupled to a portion of the line 7 between bubble trap 8 and clamp 9 may be present: if present, the bubble sensor is connected to the control unit 10 and sends to the control unit signals for the control unit to cause closure of the clamp 9 in case one or more bubbles above certain safety thresholds are detected. As shown in FIG. 2, the blood flow through the blood lines is controlled by a blood pump 11, for instance a peristaltic blood pump, acting either on the blood withdrawal line (as shown in FIG. 2) or on the blood return line.

As in the example of FIG. 1, an operator may enter a set value for the blood flow rate $Q_{BLOOD}$ through a user interface 12 and the control unit 10, during treatment, is configured to control the blood pump based on the set blood flow rate. The control unit may comprise a digital processor (CPU) and memory (or memories), an analog type circuit, or a combination thereof as explained in greater detail in below section dedicated to the 'control unit'. The control unit 10 is also connected to the user interface 12, for instance a graphic user interface, which receives operator's inputs and displays the apparatus outputs. For instance, the graphic user interface 12 may include a touch screen, a display screen and hard keys for entering user's inputs or a combination thereof.

With reference to both examples of FIGS. 1 and 2, a blood warming device 200 is associated with the apparatus 1 to form an assembly which is adapted to treat blood and keep blood within certain desired temperature boundaries. The blood warming device 200 may be an independent device (e.g. a stand alone unit physically separated from the apparatus 1) cooperating with the apparatus 1 and—in particular—warming a portion of the extracorporeal blood circuit 100. In this case, the blood warming device 200 comprises its own control system 201 and its own power supply system 202 which are respectively distinct from the power supply and from the control unit 10 of the apparatus 1. The control unit 10 of the extracorporeal blood treatment apparatus 1 is configured to communicate with the control system 201 of the blood warming device 200.

Alternatively, the warming device 200 may be a component of the apparatus 1: in this case the warming device is not an independent stand alone unit, but rather part of the apparatus 1.

In this second alternative, the power supply of the apparatus 1 may also serve and be connected to the blood warming device. Moreover, the control unit 10 directly controls the blood warming device. In particular the control unit 10 may be configured to execute at least two tasks: first, controlling operation of the extracorporeal blood treatment apparatus, and, second, controlling operation of the blood warming device.

In both cases, the blood-warming device 200 has a heating section 203 configured for receiving and heating a corresponding heated portion 102 of the extracorporeal blood circuit 100. For instance, the heated portion 102 of the blood circuit 100 may be in the form of a substantially flat bag insertable in a heating seat provided in the heating section 203 of the blood warming device. The flat bag presents an inlet and an outlet connected to the extracorporeal blood circuit. Alternatively, the heated portion 102 may include a section of the tubing or a rigid cassette inserted into the heating portion section 203 of the blood warming device 200 which for instance may comprise a heating sleeve or a heating coil wound around the tract of tubing.

The blood warming device 200 may also include a first temperature sensor 204 configured for measuring at least a blood temperature at an exit of the blood warming device and, optionally, a second temperature sensor 205 configured for measuring a further blood temperature at an entry of the blood warming device. The blood warming device further includes a power supply sensor 206 configured for measuring at least an actual electric power value supplied to (or absorbed by) the heating components of the blood warming device. Sensor 204, sensor 205 (if present) and sensor 206 are connected to the control system 201 of the blood warming device 200 or directly to the control unit 10 of the apparatus 1.

As shown in FIGS. 1, 2 and 6 the blood warming device is associated with blood circuit in correspondence of the blood return line, e.g. upstream the bubble trap 8. It may however be envisaged that the blood warming device be associated with the blood withdrawal line. In practice the heating portion 203 has heating elements (e.g. electric impedances, infrared emitters or other types of heating elements) configured to heat the corresponding heated portion 102 of the blood circuit.

The control unit 10 of the apparatus 1 is configured to establish a communication with said blood warming device 200. The communication may rely on a wired or a wireless telecommunication system and is configured such as to at least allow the control unit 10 to send commands to the blood warming device or to the blood warming device control system.

The apparatus 1 is configured to operate in a plurality of distinct operational modes and the control unit 10 is capable of identifying, e.g. at regular time intervals, the operating mode which is under execution. Once established or before having established the communication with the blood warming device, the control unit 10 may identify, among the plurality of modes of operation of the apparatus, the current operational mode, which is the mode the apparatus is performing at the instant of identification. Without being bound to a specific example, the control unit 10 may identify if the apparatus is operating in a mode wherein there is no blood flow in the extracorporeal blood circuit (e.g. in priming mode of the extracorporeal blood circuit, or if the apparatus is in fluid preparation mode of fluids to be injected in the extracorporeal circuit or to be sent to the treatment unit, or if the apparatus is in treatment interruption mode with blood pump stopped), or if the apparatus is operating in a mode wherein there is circulation of blood in the extracorporeal blood circuit (this happens for instance during treatment execution mode while delivering the therapy to a patient).

Once the current operational mode has been identified, the control unit 10 is configured to generate and issue a control signal for the blood warming device. According to an aspect of the invention the control signal comprises a command directed to impose to the blood warming device a mode of operation depending upon the identified current operational mode of the apparatus 1. In other words, the command for the blood warming device is a function of the specific operational mode of the apparatus 1 which has been identified. Thus, the command may change depending upon the specific operational mode the apparatus 1 is executing. Consider, by way of non limiting example, two operational modes: priming procedure mode and treatment execution mode; if for instance the apparatus ends the priming procedure and—after patient connection—is set to treatment execution, then the operational mode of the apparatus changes thus causing a corresponding change in the control signal. Note that a change in operational mode may take place in other circumstances, for instance:

when the user/the control unit 10 stops the treatment, or
when the user/the control unit 10 changes one or more flow rates of the blood pump, of the dialysis pump or of the infusion pumps.

The control unit then sends the control signal—via said communication—to the blood warming device 200.

Figure 3:
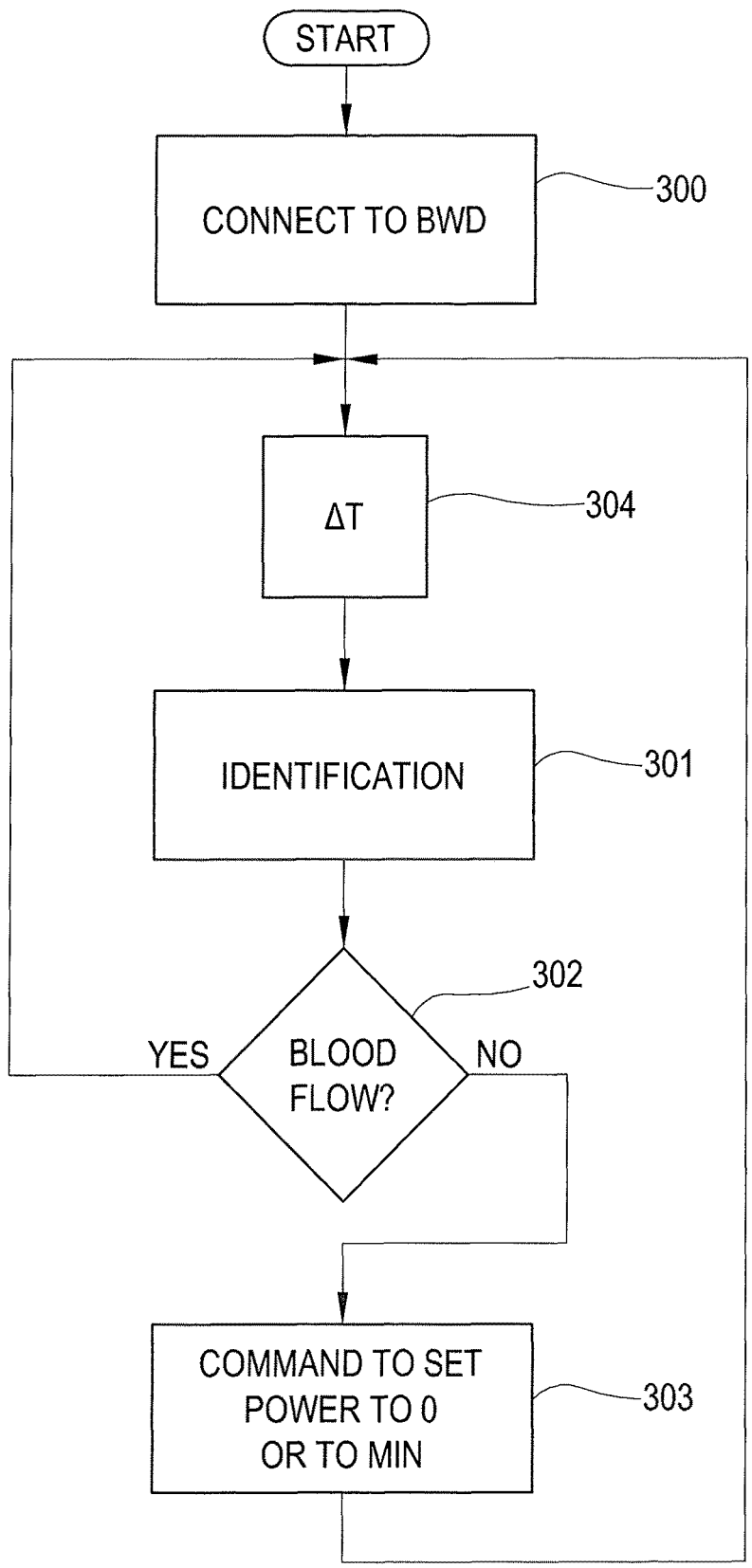
FIG. 3 shows a first flowchart of a procedure for controlling electric power supplied to the heating components of a blood warming device.
Figure 4:
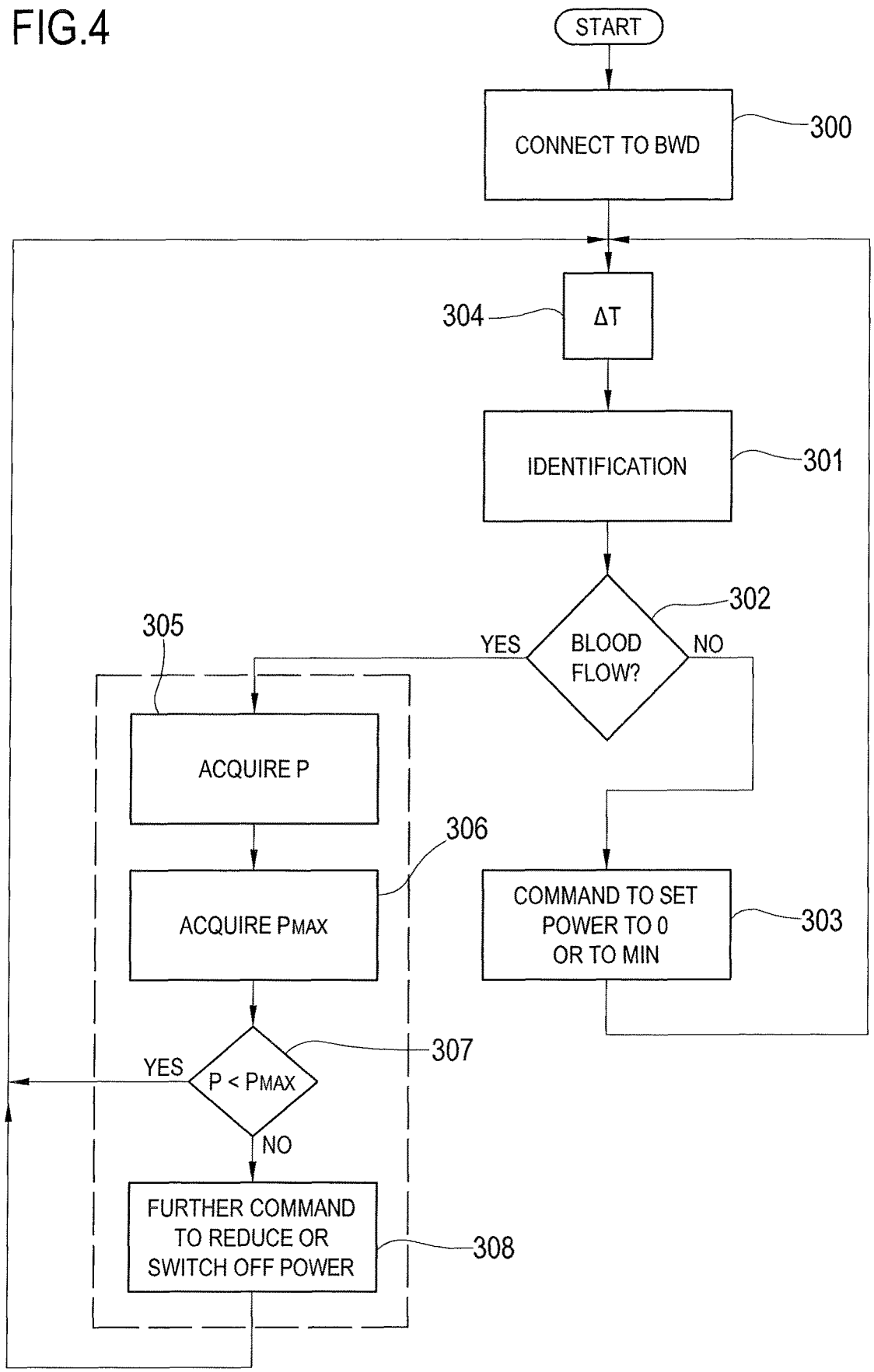
FIG. 4 shows a second flowchart of an alternative procedure for controlling electric power supplied to the heating components of a blood warming device.
Figure 5:
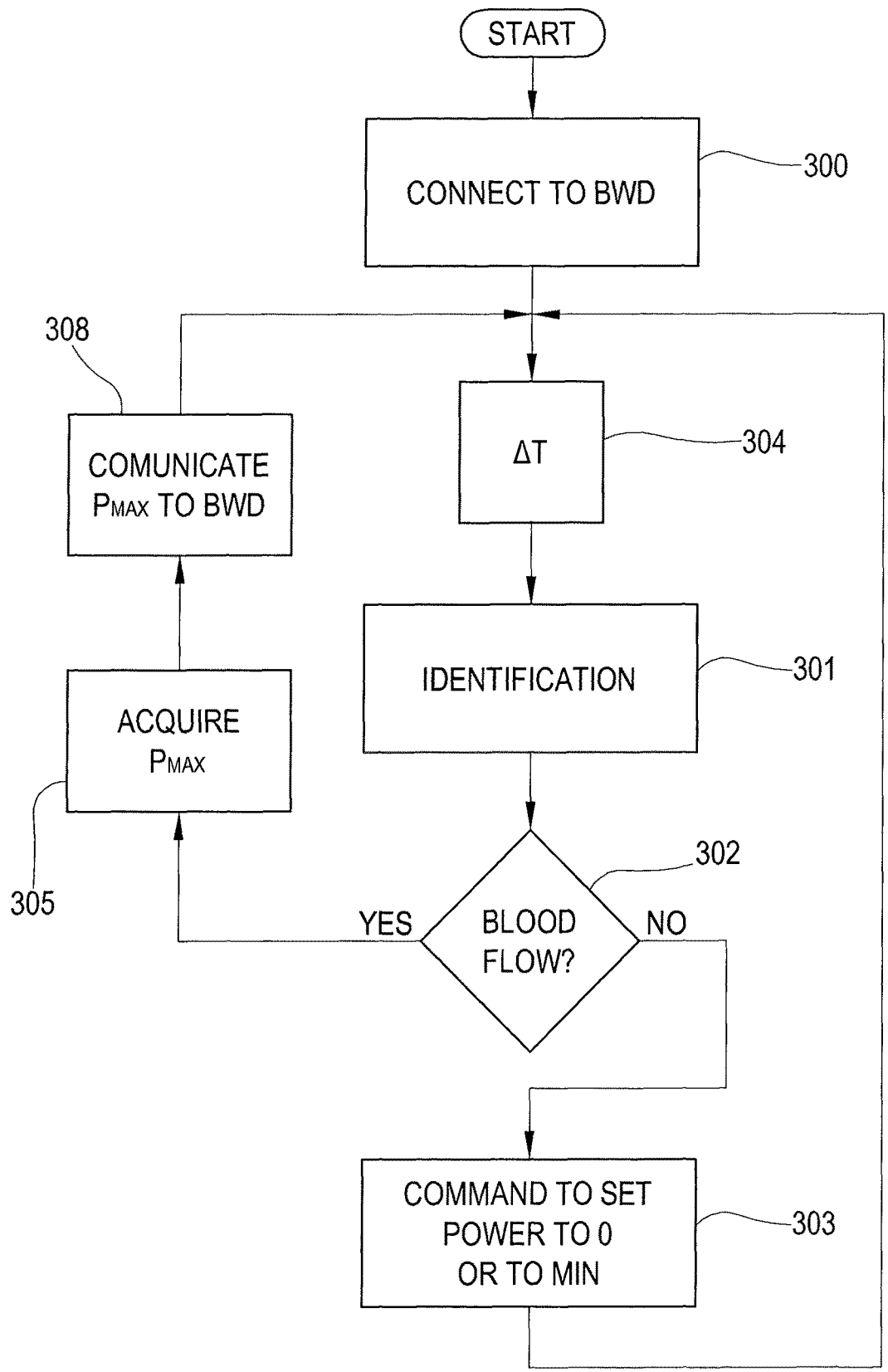
FIG. 5 shows a third flowchart of an alternative procedure for controlling electric power supplied to the heating components of a blood warming device.

With reference now to FIGS. 3-5, several alternative procedures for the control of the electric power supplied to the heating components of the blood warming device 200 are described; the procedure steps shown in the flowcharts of FIGS. 3-5 may be executable entirely by the control unit 10 or in part by the control unit 10 and in part by the control system 201 associated with the blood warming device 200. Below TABLE I schematically presents several possible configurations of the system formed by blood warming device 200 and apparatus 1: in particular for each configuration it is indicated in TABLE 1 which procedure steps are executed by control unit 10 and which are executed by control system 201.

FIG. 3 shows a first flowchart of the steps the control unit 10 of apparatus 1 may be configured to execute, in accordance with a first embodiment. The first flowchart and the steps described therein may apply to either one of the apparatus of FIGS. 1 and 2. At step 300, the control unit 10 establishes a communication with the blood warming device (BWD in FIGS. 3-5). This communication may be a unidirectional communication from control unit 10 to control system 201 or a bidirectional communication between control unit 10 and control system 201. At step 301, which may take place before or after establishing the communication, the control unit 10 carries out an identification step by checking which is the mode under current execution in the apparatus 1 (herein referred to as current operational mode). At step 302, if the identified current operational mode is a mode wherein there is no blood flow through the extracorporeal blood circuit, such as for example a treatment interruption mode (blood pump stopped or patient disconnected) or a priming mode (no blood present in blood circuit) or a fluid preparation mode (no blood present in blood circuit), then the control unit 10 is configured to generate and issue a control signal for the blood warming device 200 and to include in the control signal a command directed to (step 303):

impose the switch off of the electric power supplied at least to the heating components of the blood warming device; note this could also be done by imposing to switch the entire blood warming device off (see configuration A or D in below TABLE I); or impose that the maximum electric power allowed to be absorbed by the heating components of the blood warming apparatus is set to zero; or impose that the maximum electric power allowed to be absorbed by the heating components of the blood warming apparatus is set to a minimum threshold, different from zero (this may be the case when the patient is connected, blood is present in the extracorporeal circuit, but the blood pump has been stopped).

For instance, the above control signal including said command may be sent from the control unit 10 to the control system 201 of the warming device which then executes the command. This may be the case for instance when the apparatus 1 and the warming device 200 are two independent devices communicating to each other (see configuration A in below TABLE I). Alternatively, the control unit 10 may directly stop or drastically reduce electric power supply to the warming device 200 based on the content of the above control signal: the direct action of the control unit 10 on the device supplying power to the warming device may take place when warming device is a part integrated in the apparatus 1 (see configuration D in below TABLE I). If, instead, the identified current operational mode is a mode wherein there is blood flow in the extracorporeal blood circuit, such as for instance a treatment execution mode (or any other mode for which it is expected that the blood warming device warms blood), then the power supply to the blood warming device is neither interrupted nor set to a minimum. For instance, as shown in FIG. 3, the control unit may be configured to loop back to the identification step.

The control unit is configured to repeat the above cycle, e.g. after a certain time delay ΔT (304).

FIG. 4 shows a second flowchart of the procedure steps the control unit 10 of apparatus 1 may be configured to execute, in accordance with a second embodiment. The flowchart of second embodiment may include the procedure steps 301, 302, 303, 304 described in communication with the first embodiment (thus the description made for the first embodiment is not repeated) and certain other steps which are now described and which may be executed by control unit 10 in case, at step 302, it has been determined that the identified current operational mode is a mode wherein there is presence of blood flow. In accordance with the second embodiment of FIG. 4, in case at step 302 a mode with presence blood flow has been identified, the control unit is configured to:

acquire (step 305) the value of the electric power (herein indicated with P) absorbed by the heating components of the warming device, and control (step 306) that said electric power P allowed to be absorbed by the heating components of the blood warming apparatus does not exceed a maximum electrical power threshold (here below $P_{max}$). This maximum threshold $P_{max}$ may be predefined or it may be calculated based on the identification of the specific operating mode of the apparatus 1 (various exemplifying methods for the calculation of $P_{max}$ are disclosed herein below in a dedicated section).

In order to accomplish this control on power absorption (steps 305 and 306), the electrical power P may be measured by appropriate means on the warming device (e.g., sensor 206) and communicated by control system 201 to control unit 10, or the electrical power P may be measured by appropriate means directly connected to control unit 10. Once the control unit has acquired the value of the electrical power P and of maximum threshold $P_{max}$, the control unit 10 is configured to compare P with maximum threshold $P_{max}$. If $P<P_{max}$ the control unit may be configured to simply loop back to the identification step, e.g. after a certain time delay ΔT (304). If instead $P_{max}$ the control unit may be configured to generate and issue a further control signal for the blood warming device 200 and to include in the control signal a command directed to impose a reduction, or a switch off, of electric power supply at least to the heating components of the blood warming device (see configuration B in below TABLE I). For instance, the above control signal including said command may be sent to by the control unit 10 to the control system 201 of the warming device: this may be the case for instance when the apparatus 1 and the warming device 200 are two independent devices in communication with each other (see configuration B in below table 1). The control signal is then received by the control system 201 which, on its turn, is configured to execute the command included in the control signal.

Alternatively, the control unit 10 may directly stop or reduce electric power supply to the heating components of the warming device: the direct action of the control unit 10 on the power supplied to the warming device may take place when warming device is a part integrated in the apparatus 1 (see configuration E in below TABLE I). FIG. 5 shows a third flowchart of the procedure steps the control unit 10 of apparatus 1 may be configured to execute, in accordance with a third embodiment. The third flowchart and the procedure steps described therein may apply to either one of the apparatus of FIGS. 1 and 2. In accordance with the third embodiment of FIG. 5 the control unit may be configured to execute the steps 300, 301, 302, 303 and 304 as disclosed in connection with the first embodiment of FIG. 3 (thus the description made for the first embodiment is not repeated) and certain other steps which are now described and which may be executed by control unit 10 in case, at step 302, it has been determined that the identified current operational mode is a mode wherein there is presence of blood flow.

In accordance with the third embodiment of FIG. 5, in case at step 302 a mode with presence of blood flow has been identified, the control unit 10 is configured to calculate (step 306) a maximum electrical threshold $P_{max}$ allowed to be absorbed by the heating components of the warming device 200 at least based on the identification of the specific operating mode of the apparatus 1: details of possible ways of calculating $P_{max}$ are given in a separate section below. For instance the maximum threshold $P_{max}$ may be calculated based on the total flow rate of the fluids exchanged by the apparatus 1 during the treatment. Note that in accordance with a possible variant it may also be envisaged that the control unit is configured to allow an operator entering a value for said maximum threshold $P_{max}$ via user interface 12 (this can be additional or alternative to the computation of said maximum threshold $P_{max}$ based on the total flow rate of fluid exchanged with the blood).

Once $P_{max}$ has been calculated or received by the control unit 10, the control unit 10 is also configured to communicate $P_{max}$ to the control system 201 of the warming device 200 (step 309). The control system 201 is then configured to receive said value $P_{max}$ and to make sure that the power P absorbed by the heating components of the warming device is maintained below said maximum threshold $P_{max}$ (configuration C in below TABLE I). In practice, in accordance with this embodiment, it is the control system 201 configured to compare P with maximum threshold $P_{max}$ and if $P \geq P_{max}$ to impose a reduction, or a switch off, of electric power supply at least to the heating components of the blood warming device.

Below TABLE I schematically recaps the main features and the main actions taken by the control unit 10 and by the control system 201 for several alternative, and non limiting, embodiments of the warmer and apparatus according to aspects of the invention.

TABLE I

| Config | Warmer device 200 separate from apparatus 1? | Warmer control system 201 actions | Required communication to apparatus 1 | Power measurement | Control unit 10 actions |
|---|---|---|---|---|---|
| A | YES | none | Required communication at least from control unit 10 to control system 201 | No | Generates and sends to control system 200 control signal with command to set warmer heating components ON/OFF depending upon outcome of identification step |
| B | YES | Transfer P value to control unit 10 | Bidirectional communication from control unit 10 to control system 201 AND from control system 201 to control unit 10 | Yes, for instance sensor 206 | Generates and sends to control system 201 control signal with command to set warmer heating components ON/OFF depending upon outcome of identification step Generates and sends to control system 201 further control signal with command to set warmer OFF if P > Pmax |
| C | YES | Controls P < Pmax | Required communication at least from control unit 10 to control system 201 | Yes, for instance sensor 206 | Generates and sends to control system 201 control signal with command to set warmer heating components ON/OFF depending upon outcome of identification step Pmax calculation and transfer of Pmax to 201 |
| D | NO: warmer device 200 integrated in apparatus 1 | N/A | N/A | No | Sets warmer heating components ON/OFF depending upon outcome of identification step |
| E | NO: warmer device 200 integrated in apparatus 1 | N/A | N/A | Yes, for instance sensor 206 | Sets warmer heating components ON/OFF depending upon outcome of identification step Pmax calculation and control P < Pmax |

A. Determination of the Maximum Threshold $P_{max}$

In the case where the maximum threshold $P_{max}$ is a calculated value, the control unit may be configured to calculate said maximum threshold at least based on one or more of the following flow rates:

a dialysate flow rate $Q_{DIAL}$ which is a preset or measured value of flow through said fresh dialysate line, a pre-infusion flow rate $Q_{REP1}$ which is a preset or measured value of flow through said pre-infusion line, a post-infusion flow rate $Q_{REP2}$ which is a preset or measured value of flow through said post-infusion line, a pre-blood pump infusion flow rate $Q_{PBP}$, which is a preset or measured value of flow through said pre-blood pump infusion line, an effluent flow rate $Q_{EFF}$ which is a preset or measured flow rate through the effluent line.

Note that in accordance with a preferred mode, all the non zero fluid flow rates injected in blood and exchanged in the blood treatment unit are considered in the computation as well as their respective temperatures. Furthermore, the control unit 10 may also optionally be configured to calculate said maximum threshold $P_{max}$ based also on said flow of blood $Q_{BLOOD}$, although blood flow rate has normally a lower impact on the computation compared to the flow rates $Q_{DIAL}$, $Q_{REP1}$, $Q_{REP2}$, $Q_{PBP}$ of the fluids exchanged in the apparatus during treatment.

The control unit 10 may, in accordance with a further variant, be configured to receive the room temperature value, which is the temperature in the room where the treatment is taking place, and a fluid temperature values of the fluids circulating in one or more of the fresh dialysate line, pre-infusion line, post-infusion line, a pre-blood pump infusion line. The room temperature value may be a measured value or a set value entered by the user or a preset value stored in the control unit (e.g. 24° C.). Each of the fluid temperature value(s) may be a measured temperature value or a set temperature value entered by the user or preset in the control unit (e.g. 23° or 24° C.). Furthermore, the control unit 10 may receive a set value for the temperature desired in the blood and, optionally, measured value(s) for the actual blood temperature (e.g. a temperature value as measured by the first and/or second sensor 204, 205 in correspondence of the entry and/or the exit of the blood warming device 200).

Then, the control unit may be configured to calculate said maximum threshold $P_{max}$ of power allowed to be supplied to the heating components at least based on:
- the desired blood temperature, namely the blood temperature at which it is desired to bring blood returning to patient,
- the fluid temperature values of the fluid fed to the fresh dialysate line, pre-infusion line, post-infusion line, pre-blood pump infusion line, and any other line connected to the blood circuit,
- each of the values of the non zero fluid flow rates injected into the extracorporeal blood circuit or exchanged with the blood treatment unit 2; depending upon the configuration of the apparatus 1 these flow rates may include one or more of: dialysate flow rate $Q_{DIAL}$, pre-infusion flow rate $Q_{REP1}$, post-infusion flow rate $Q_{REP2}$, a pre-blood pump infusion flow rate $Q_{PBP}$, the flow rate of any other line connected to the extracorporeal blood circuit
- a warmer efficiency coefficient η relating electrical consumption of the heating elements to the heat power transferred to the blood. This coefficient might be a function of other known parameters (e.g. power consumption) and is characteristic of the warmer unit.

A.1. Models for the Determination of the Maximum Threshold $P_{Max}$

Here below two examples are provided of mathematical models for the computation of the maximum electrical power consumption allowed to the heating elements (i.e. the maximum threshold) of the blood warmer. The following definitions and notations are used:

$P_{heat}$: heating power delivered to the fluid
$P_{cons}$: electrical power consumption of the warmer heating elements
$P_{max}$: maximum electrical power consumption allowed to the warmer (maximum threshold)
$Q_{BLOOD}$: blood flow rate
$Q_{EXCH}=Q_{PBP}+Q_{DIAL}+Q_{REP}$: total fluid exchange flow rate
$Q_{PBP}$: pre-blood pump infusion flow rate
$Q_{DIAL}$: dialysate flow rate
$Q_{REP}$: replacement infusion flow rate (pre or post are respectively indicated as $Q_{REP1}$ and $Q_{REP2}$ where $Q_{REP}=Q_{REP1}+Q_{REP2}$)
$Q_{PFR}$: patient fluid removal rate
$T_{room}$: room temperature
$T_{fluid}$: solution bag or fluid temperature
$T_{eff}$: effluent temperature
$T_{bi}$: blood temperature at location I (see FIG. 8)
$\eta P_{heat}/P_{cons}$: warming yield of the warmer
ρ: fluid density
Cp: specific heat
k: adjustment coefficient
p: heat loss coefficient to atmosphere (for blood tubing)

A.2. Example 1 (FIG. 7)

Figure 7:
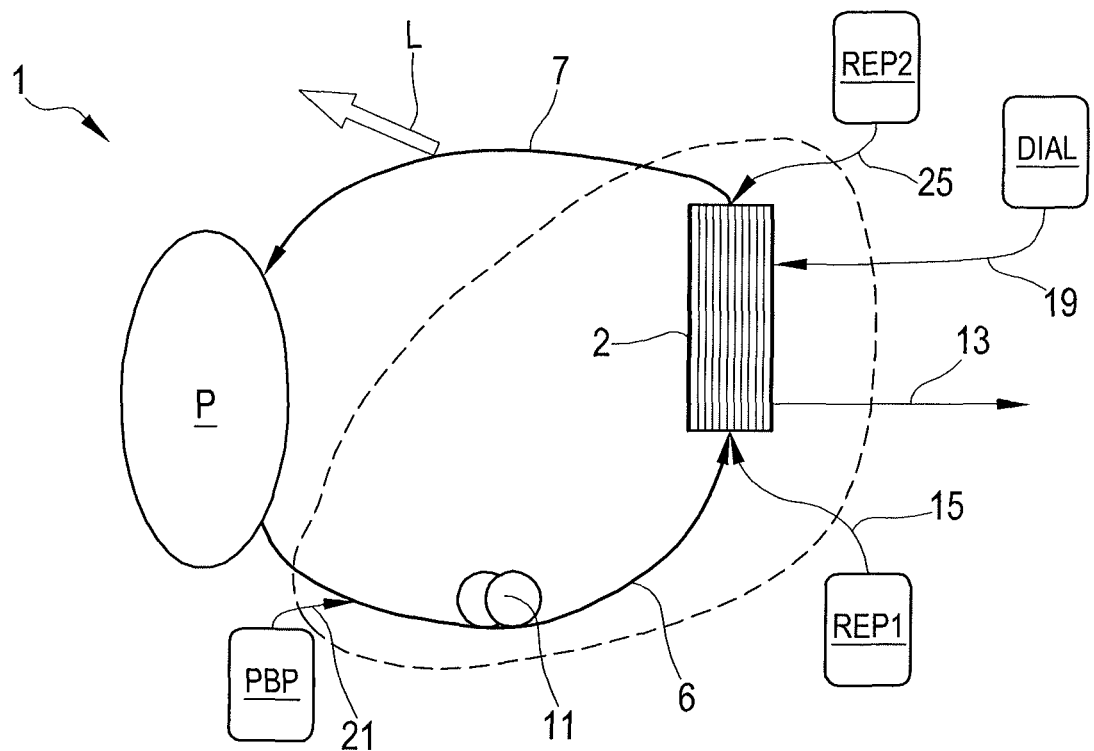
FIG. 7 shows an illustration of a first model for calculating heat loss to estimate the power that should be transferred to the patient blood to balance the heat losses to atmosphere.

For this first example of computation, reference is made to FIG. 7 illustrating a schematic model for heat loss computation. In FIG. 7 the patient is schematically represented with block P. Also note that in FIG. 7, the same reference numerals used in FIG. 1 have been adopted for same components in order to avoid repetitions; arrow L schematically represents in FIG. 7 the heat losses to atmosphere. In this first example of computational model it is minimized the number of parameters used to get a reliable estimation of the power that should be transferred to the patient blood to balance the heat losses to atmosphere.

Equations

Heat losses to atmosphere are taken as a constant:

$$P_{loss\_atm}=25 \text{ W} \qquad \text{Eq.A1}$$

Heat losses due to fluid exchange are computed as:

$$P_{loss\_exch}=\rho \times Cp \times Qexch \times (T_{eff}-T_{fluid}) \qquad \text{Eq.A2}$$

Where ρ·Cp=4.18 J/° C./ml is constant
$T_{eff}$=36° C. is taken as constant
$T_{fluid}$=23° C. is taken as constant, or can be requested to the operator.

In order to get a therapy with no heat loss or gain, following equation shall be verified:

$$P_{heat}=P_{loss\_atm}+P_{loss\_exch} \qquad \text{Eq.A3}$$

Considering that the blood warmer is not perfect and uses more electrical power than the heat power transferred to the circulating fluid, the electrical power required to deliver $P_{heat}$ is such as:

$$P_{cons} = \frac{P_{heat}}{\eta} \qquad \text{Eq.A4}$$

Maximum allowed power to the heating elements may be adjusted by a fixed coefficient k:

$$P_{max}=k \times P_{cons} \qquad \text{Eq.A5}$$

Equation for heat losses due to fluid exchange overestimates heat losses as effluent temperature is below 36° C. in most circumstances. As a matter of fact both heat losses to atmosphere in the access line and cooling effects of the infusions occurring upstream the CRRT filter lead to a blood temperature below 36° C. at the filter inlet. Effluent temperature is at most equal to blood inlet temperature at the filter.

Patient fluid removal is not included in the definition of the total fluid exchange rate as the associated amount of heat loss matches with a net patient fluid loss. Accordingly patient temperature is kept constant if equation 3 is verified, while it would be increased if fluid removal was included in the computation of $P_{loss\_exch}$.

Warmer yield with respect to power consumption q is per definition below 1.0. This parameter is also not constant over the warmer operating range, and can be typically expressed as a function of the power consumption $P_{cons}$ or transferred heat power $P_{heat}$; in this way, equation 4 might be implicit and require an iterative computation process.

Adjustment coefficient k is typically taken as 1,0. Values larger than 1,0 can be considered in the case constant parameters chosen in equations 1 and 2 may not cover some extreme situations and that designer wants to avoid situations were blood warming is limited due to an underestimated $P_{max}$ value.

Numerical Application
Input Data
A CRRT therapy is performed in following conditions:
$Q_{EFF}$=3200 ml/h
$Q_{PFR}$=100 ml/h
No information is available on the room temperature.
Power yield of the warmer is documented as:

$$\eta = \frac{15 + 1.1 \times P_{heat}}{P_{heat}}$$

Adjustment coefficient is taken as: k=1.
$P_{max}$ Computation
Fluid exchange rate is defined as:

$Q\text{exch} = Q\text{eff} - Q\text{pfr} = 3200 - 100 = 3100$ ml/h

From equation A2:

$P_{loss\_exch} = 4.18 \times 3100/3600 \times (36-23) = 46.8$ W

From equation A3:

$P_{heat} = 25 + 46.8 = 71.8$ W

From equation A4:

$$P_{cons} = \frac{P_{heat}}{\eta(P_{heat})} = 15 + 1.1 \times 71.8 = 94.0 W$$

From equation A5:

$P = 1.0 \times P_{cons} = 94.0$ W

Figure 8:
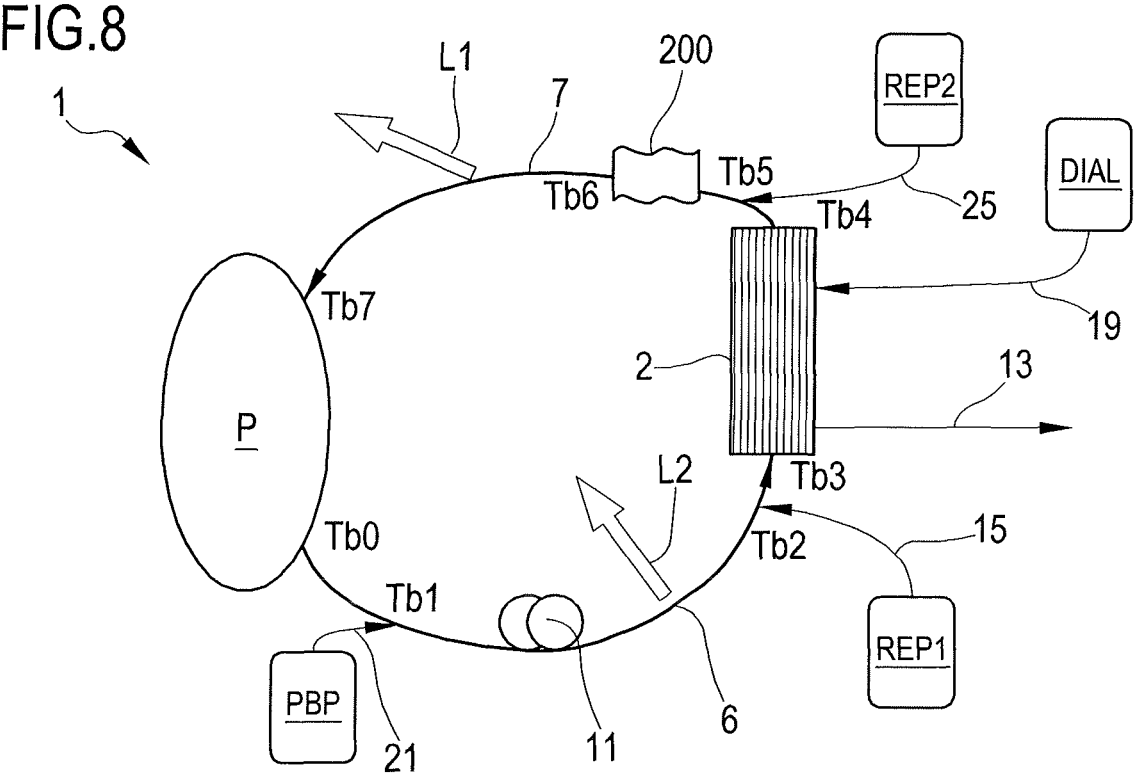
FIG. 8 shows an illustration of a second model for calculating heat loss to estimate the power that should be transferred to the patient blood to balance the heat losses to atmosphere.

A.3 Example 2 (FIG. 8)

For this second example of computation, reference is made to FIG. 8 illustrating a further model for heat loss computation. The patient is schematically represented with block P. Also note that in FIG. 8, the same reference numerals used in FIG. 1 have been adopted for same components in order to avoid repetitions; arrows L1 and L2 schematically represent in FIG. 7 the heat losses to atmosphere of the withdrawal line 6 and of the return line 7. In this second example of computational model equations are used as to more accurately evaluate:

the heat losses to atmosphere of the withdrawal and return lines,
the effluent temperature and the losses due to fluid exchange at the various mixing points and at the treatment unit.

Heat losses to atmosphere of the treatment unit will be neglected.

The temperatures as represented in FIG. 8 are identified as follows:
Patient temperature: $T_{b0}$
Blood temperature after PBP infusion: $T_{b1}$
Blood temperature after heat losses to atmosphere from withdrawal line: $T_{b2}$
Blood temperature after pre-replacement infusion: $T_{b3}$
Filter outlet temperature after dialysate exchange: $T_{b4}$
Blood temperature after post-replacement infusion: $T_{b5}$
Blood temperature at warmer device outlet: $T_{b6}$
Blood return temperature: $T_{b7}$ Equations
a) Determination of Heat losses to Atmosphere
Assuming heat losses to atmosphere are driven by convection, evolution of temperature along a tube 'immersed' in atmosphere at temperature $T_{room}$ for a fluid flowing at rate Q can be expressed as:

$$\rho \times Cp \times Q \times \frac{dT}{dx} = p \times (T(x) - T_{room}) \quad \text{local equation} \qquad \text{Eq.B1}$$

$$T(L) = T_{room} + (T(0) - T_{room}) \times \exp^{-\frac{p \times L}{\rho \times Cp \times Q}}$$

Where x is associated with tube axis
x=0 is tube inlet
x=L is tube outlet
L is the tube length
p is a heat loss coefficient in W/° C./m
General equation B1 may be directly used for estimating heat losses in the withdrawal and return lines.

Next table identifies the parameters to be used in equation B1 for each piece of the blood circuit.

| Circuit section | Temperature condition | Flow rate Q | Tubing length L |
|---|---|---|---|
| Access line | T(0) = Mixing temperature* between blood and PBP infusion (Tb1) | $Q_{BLOOD} + Q_{PBP}$ | Access line length |
| Return line | T(L) = 37° C.: blood returned at patient temperature | $Q_{BLOOD} - Q_{PFR}$ | Return line length |

*calculation of temperatures at mixing points is explained below

The above model for calculation of heat losses to atmosphere provides very good results still relying on a relatively simple set of equations. Note that in the above model heat loss coefficients of access and return lines are assumed to be identical as the same physical tube is used for these two pieces of the blood circuit. Computation of heat losses on the return line assumes that the blood warmer is able to balance all heat losses occurring in the blood circuit upstream the blood warmer, as well as to deliver slight over-warming as to compensate for blood cooling in the return line. Of course, even more sophisticated models could be conceived, which may for instance include additional equations for estimating heat losses to atmosphere of the filter/dialyzer.

b) Calculation of Heat Losses Related to Fluid Exchange b.1) Blood temperature at mixing points between blood and infusions Resulting blood temperature is the 'mixing' temperature of the two fluids, which can be computed according to formula:

$$\rho_1 \times Cp_1 \times Q_1 \times T_1 + \rho_2 \times Cp_2 \times Q_2 \times T_2 = \rho_3 \times Cp_3 \times (Q_1 + Q_2) \times T_3 \qquad \text{Eq.B2}$$

Where index 1 and 2 refers to fluid 1 and 2, respectively and index 3 refers to resulting mixture of the two fluids.

Assuming that all $\rho_i \times Cp_i$ are identical, equation B2 simplifies into:

$$T_3 = \frac{Q_1 \times T_1 + Q_2 \times T_2}{Q_1 + Q_2} \qquad \text{Eq.B3}$$

Below table shows how to compute mixing temperature using B3 equation

| Infusion site | Blood circuit | | Infusion | |
|---|---|---|---|---|
| | Flow rate | Temperature | Flow rate | temperature |
| PBP | $Q_{BLOOD}$ | Patient temperature $T_{b0}$ | $Q_{PBP}$ | $T_{fluid}$ |
| Pre-filter infusion | $Q_{BLOOD} + Q_{PBP}$ | Temperature after PBP mixing and access line heat losses $T_{b2}$ | $Q_{REP1}$ | $T_{fluid}$ |
| Post-filter infusion | $Q_{BLOOD} - Q_{REP2} - Q_{PFR}$ | Temperature at filter outlet $T_{b4}$ | $Q_{REP2}$ | $T_{fluid}$ | b.2) Blood Temperature at the Blood Treatment Unit in Presence of Dialysate

Hemodialyzers or filters used as blood treatment unit 2 are good heat exchangers; moreover in view of the flow rate conditions of CRRT therapies, effluent outlet temperature can be considered in equilibrium with the inlet blood temperature ($T_{b3}$). With this assumption, outlet filter temperature $T_{b4}$ can be derived from the heat balance equation across the hemodialyzer or filter.

Assuming that $\rho \cdot Cp$ has same value for all fluids, the following Equation (Eq. B4) is obtained:

$$(Q_{BLOOD} + Q_{PBP} + Q_{REP1}) \times T_{b3} + Q_{DIAL} \times T_{fluid} = (Q_{BLOOD} - Q_{REP2} - Q_{PFR}) \times T_{b4} + Q_{EFF} \times T_{b3}$$

which gives:

$$T_{b4} = T_{b3} - [Q_{DIAL} \times (T_{b3} - T_{fluid})/(Q_{BLOOD} - Q_{REP2} - Q_{PFR})] \qquad \text{Eq.B5}$$

It should be noted that, in principle, it could be possible to consider the slight differences in both density and specific heat of blood and infusion fluids, as well as dependence of these parameters on haematocrit for the blood. However the resulting adjustments are of limited interest in the context of Pmax definition. By default patient temperature is taken as 37° C.

b.3) Determination of Heat Loss Power

Previous equations describe evolution of temperature along the circuit.

Heat losses power is thereby derived from computed temperatures:

$$P_{heat} = \rho \times Cp \times (Q_{BLOOD} - Q_{PFR}) \times (T_{b0} - T_5) + \rho \times Cp \times (Q_{BLOOD} - Q_{PFR}) \times (T_{b6} - T_{b7}) \qquad \text{Eq.B6}$$

Note heat losses related to patient fluid removal are ignored.

Once $P_{heat}$ is calculated, then the maximum threshold $P_{max}$ may be determined using known equations, e.g. of the type of equations A.4 and A.5 above.

As a general rule, max power computation shall consider that warming prescription can cover situations where net patient warming is desired, meaning that return temperature $T_{b7}$ is higher than patient temperature $T_{b0}$.

Numerical Application

Input Data

A CRRT therapy is performed in following conditions:

$Q_{BLOOD}$=180 ml/min
$Q_{PBP}$=700 ml/h
$Q_{DIAL}$=2000 ml/h
$Q_{REP2}$=200 ml/h
$Q_{PFR}$=100 ml/h Room and fluid temperature is 24° C.

Assumption and System Parameters

Patient temperature $T_{b0}$ is 37° C.; possibility to deliver return temperature $T_{b7}=T_{b0}+1°$ C. is considered.

Known parameters for computation of heat losses to atmosphere are:

p=0.40 W/° C./m
Withdrawal line length: 2.5 m
Return line length: 2.8 m
Power yield of the warmer is documented as:

$$\eta = \frac{15 + 1.1 \times P_{heat}}{P_{heat}}$$

Adjustment coefficient is taken as: k=1.1

$P_{max}$ Computation $T_{b0}$=37.0° C.
$T_{b1}$=36.21° C. after PBP infusion (from equation B3)
$T_{b2}$=35.33° C. after heat losses along access line (from equation B5)
$T_{b3}=T_{b2}$ as no pre-replacement infusion
$T_{b4}$=33.17° C. after heat exchange with dialysate (from equation B1)
$T_{b5}$=33.00° C. after post-replacement infusion (from equation B3)
$T_{b7}$=38.0° C. as return blood temperature
$T_{b6}$=39.32° C. as required temperature at warmer outlet to balance heat losses of return line (from equation B1)

$$P_{heat} = 4.18 \times (180 - 1.7) \times$$
$$[(37.00 - 33.00) + (39.32 - 38.00)] = 78.5W \quad \text{(from eq.B6)}$$

$$P_{cons} = \frac{P_{heat}}{\eta(P_{heat})} = 15 + 1.1 \times 78.5 = 101W$$

$$P_{max} = 1.1 \times P_{cons} = 111W.$$

The invention also concerns methods of controlling the electric power P supplied to the heating components of a blood-warming device active on an extracorporeal blood circuit of an extracorporeal blood treatment apparatus. The apparatus may be one of the type according to any one of the enclosed apparatus. In particular, the apparatus may be one of those described above and depicted in FIGS. 1 and 2.

The method of controlling supplied electric power P, which may be executed by a control unit part of the blood treatment apparatus 1 or in part by control unit 10 and in part by control system 201, comprises the steps described above in connection with FIG. 3 or FIG. 4 or FIG. 5. The method may also include the steps disclosed in connection above section A for the determination of the maximum threshold $P_{max}$ which are therefore not repeated.

Control Unit 10 and Control System 201

As already indicated the apparatus 1 according to the invention makes use of at least one control unit 10. The blood warming device, if separate from the apparatus 1, also includes at least one control system 201. The control unit 10 and—if present—the control system 201 may comprise a respective digital processor (CPU) with memory (or memories), an analog type circuit, or a combination of one or more digital processing units with one or more analog processing circuits. In the present description and in the claims it is indicated that the control unit and, respectively, the control system are "configured" or "programmed" to execute certain steps: this may be achieved in practice by any means which allow configuring or programming the control unit and, respectively, the control system. For instance, in case of a control unit or control sysem comprising one or more CPUs, one or more programs are stored in an appropriate memory: the program or programs containing instructions which, when executed by the control unit, respectively the control system—cause the control unit or the control system to execute the steps described or claimed in connection with the control unit or in connection with the control system. Alternatively, if the control unit, or respectively the control system, is of an analog type, then the circuitry of the control unit, or respectively of the control system, is designed to include circuitry configured, in use, to process electric signals such as to execute the control unit or control system steps herein disclosed.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. An extracorporeal blood treatment apparatus comprising:
   a holding portion configured for receiving an extracorporeal blood circuit having a treatment unit, a blood withdrawal line connected to a blood inlet of the treatment unit, and a blood return line connected to an outlet of the treatment unit;
   a blood pump which, when the extracorporeal blood circuit is received by the holding portion, is configured for controlling the flow of blood flowing through at least one of said blood withdrawal line and blood return line;
   at least one treatment fluid source;
   at least one treatment fluid line in fluid communication with the at least one treatment fluid source and in direct or indirect fluid communication with said extracorporeal blood circuit to supply treatment fluid to the extracorporeal blood circuit; and
   a control unit connectable with a blood warming device having heating components, the control unit being configured to execute a control procedure for the blood warming device to heat and maintain at least a portion of the extracorporeal blood circuit within a desired temperature boundary, wherein the control procedure includes:
      establishing a communication with said blood warming device,
      identifying, among a plurality of modes of operation of the apparatus, a current operational mode which the apparatus is performing,
      calculating an electric power maximum threshold allowed to be supplied to the heating components of the blood-warming device, wherein the power maximum threshold is calculated based at least on measured or set flow rates of the treatment fluid from the at least one treatment fluid source in said at least one treatment fluid line, and
      generating a control signal for the blood warming device based on the calculated electric power maximum threshold, the control signal comprising at least one of the following:
         a command directed to impose to the blood warming device a mode of operation and an amount of electric power to be supplied to the heating components of the blood warming device depending upon the identified current operational mode of said apparatus; or
         an information defining said identified current operational mode.

2. The apparatus of claim 1, wherein the control signal comprises both a command directed to impose to the blood warming device a mode of operation depending upon the identified current operational mode of said apparatus, and information defining said identified current operational mode.

3. The apparatus according to claim 1, wherein identifying the current operational mode of the apparatus comprises checking whether or not the mode of current operation of the apparatus is a mode wherein there is no blood flow through the extracorporeal blood circuit.

4. The apparatus according to claim 1, wherein identifying the current operational mode of the apparatus comprises checking whether or not the mode of current operation of the apparatus is a mode wherein the extracorporeal blood circuit is connected to a patient cardiovascular system.

5. The apparatus according to claim 1, wherein the step of generating a control signal in said control procedure comprises:
   if the identified current operational mode of the apparatus is a mode where there is no blood flow through the extracorporeal blood circuit or a mode wherein the extracorporeal blood circuit is not connected to a patient cardiovascular system, then configuring said command to impose a switching-off of electric power to at least the heating components of the blood warming device.

6. The apparatus according to claim 1, wherein the control procedure further comprises receiving at least a power information signal including information related to the electric power supplied to the heating components of said blood warming device.

7. The apparatus according to claim 1, wherein when the control signal includes the command, the step of generating a control signal in said control procedure comprises:
   if the identified current operational mode of the apparatus is a mode wherein there is no blood flow through the extracorporeal blood circuit or a mode wherein the extracorporeal blood circuit is not connected to a patient cardiovascular system, then
   configuring said command to:
      impose that the electric power supplied to the heating components of the blood-warming apparatus be set to zero; or impose that the electric power supplied to the heating components of the blood-warming apparatus be set to a minimum, different from zero.

8. The apparatus according to claim 1, wherein if the current operational mode is a mode wherein there is presence of blood flow in the extracorporeal blood circuit, the control procedure comprises repeating at least the identification step, either after a certain time delay from a preceding identification step or after detection of a change in the operating mode of said apparatus.

9. The apparatus according to claim 1, wherein the step of generating a control signal in said control procedure comprises the following:
if the identified current operational mode is a mode wherein there is presence of blood flow in the extracorporeal blood circuit, the control unit is configured to include in the control signal a further command which is directed to impose that electric power supplied to the heating components of the blood warming device be below said maximum threshold.

10. The apparatus according to claim 1, comprising the extracorporeal blood circuit with the treatment unit having a semipermeable membrane dividing the same treatment unit into a blood or primary chamber and a dialysate or secondary chamber, wherein said at least one treatment fluid line of the apparatus comprises one or more in the group of:
a fresh dialysate line connected to a dialysate inlet of said dialysate or secondary chamber,
a pre-infusion line connected to said blood withdrawal line downstream said blood pump,
a post-infusion line connected to said blood return line, downstream said blood-warming device,
a pre-blood pump infusion line connected to said blood withdrawal line upstream said blood pump,
a waste line connected to an outlet of said dialysate or secondary chamber; and
wherein the maximum threshold is calculated based at least on one or more of the following flow rates:
a dialysate flow rate which is a set or measured value of flow through said fresh dialysate line,
a pre-infusion flow rate which is a set or measured value of flow through said pre-infusion line,
a post-infusion flow rate which is a set or measured value of flow through said post-infusion line,
a pre-blood pump infusion flow rate, which is a set or measured value of flow through said pre-blood pump infusion line, or
an effluent flow rate which is a set or measured flow rate through an effluent line.

11. The apparatus according to claim 1, wherein the control procedure includes calculating an electric power maximum threshold at least as a function of the set or measured flow rates through one or more of the following lines:
a fresh dialysate line connectable to a dialysate chamber of the treatment unit,
a pre-infusion line connectable to the blood withdrawal line,
a post-infusion line connectable to the blood return line,
a pre-blood pump infusion line connectable to the blood withdrawal line, or
a waste line connectable to an outlet of the dialysate chamber of said treatment unit;
wherein generating the control signal comprises configuring said control signal to include one or both of:
a command directed to impose to the blood warming device said maximum threshold as maximum electric power allowed to be supplied to the heating components of the blood warming device, or
the calculated value of said maximum threshold.

12. The apparatus according to claim 1, wherein the control procedure further includes:
receiving from the blood warming device at least a power information signal indicative of the electric power currently supplied to the heating components of the blood warming device,
comparing said supplied electric power against said maximum threshold, and if it is detected that the supplied electric power is greater or equal to said maximum threshold, configure said command included in the control signal to:
reduce the electrical power supplied to the heating components of the blood-warming device, and setting said supplied electric power to zero; or
switch off the blood warming device.

13. The apparatus according to claim 1, wherein the maximum threshold is calculated based at least on non-zero fluid flow rates injected in blood and exchanged in the blood treatment unit.

14. The apparatus according to claim 1, wherein the maximum threshold is calculated at least based on non-zero fluid flow rates and on respective temperatures of the fluids exchanged by the apparatus during the treatment through one or more of a fresh dialysate line, a pre-infusion line, a post infusion line, a pre-blood pump infusion line, and a waste line.

15. The apparatus according to claim 14, wherein the maximum threshold is calculated based also on said flow of blood.

16. The apparatus according to claim 14, wherein the maximum threshold is calculated based also on a room temperature value, which is the value of temperature in the room where the treatment is taking place with the apparatus, said room temperature value being a measured value or a set value entered by a user or a preset value stored in the control unit.

17. The apparatus according to claim 1, wherein the control procedure comprises receiving a set value for a temperature desired in the blood returning to patient and calculating said maximum threshold also based on said desired blood temperature value.

18. The apparatus according to claim 1, wherein the maximum threshold is calculated based at least on:
a desired blood temperature value,
the fluid temperature values of fluid fed to a fresh dialysate line, pre-infusion line, post-infusion line, pre-blood pump infusion line, or any other line connected to the blood circuit, and
each of the values of non-zero fluid flow rates injected into the extracorporeal blood circuit or exchanged with the blood treatment unit.

19. The apparatus according to claim 18, wherein the values of the non-zero fluid flow rates injected into the extracorporeal blood circuit or exchanged with the blood treatment unit comprise one or more of: dialysate flow rate, pre-infusion flow rate, post-infusion flow rate, pre-blood pump infusion flow rate, or a flow rate of any other line connected to the extracorporeal blood circuit.

20. The apparatus according to claim 18, wherein the maximum threshold is calculated additionally based on:
a warmer efficiency coefficient $\eta$ relating electrical consumption of the heating components to heat power transferred to the blood.

21. An assembly including the extracorporeal blood treatment apparatus according to claim 1 and the blood warming device, wherein the blood warming device includes a heating section provided with the heating components, and which is configured for receiving and heating a corresponding portion of the extracorporeal blood circuit.

22. The assembly according to claim 21 wherein the blood warming device and the extracorporeal blood treatment apparatus are separate, the blood warming device comprising:
a respective power supply system separate from that of the apparatus,
a respective control system separate from the apparatus control unit,
the extracorporeal blood treatment apparatus communication to the blood warming device comprising a communication, between the control unit of the extracorporeal blood treatment apparatus and the control system of the blood warming device wherein the control system of the blood warming device is configured to:
receive the control signal, and
execute said command.

23. The assembly according to claim 21 wherein the blood warming device is a component part of the extracorporeal treatment apparatus, and the control unit of the apparatus includes a control system of the warming device and is configured to execute:
a first task comprising said control procedure, and
a second task comprising:
receiving the control signal, and
executing said command.

24. The assembly according to claim 21, wherein the blood warming device and the extracorporeal blood treatment apparatus are separate, the blood warming device comprising:
a respective power supply system separate from that of the apparatus,
a respective control system separate from the apparatus control unit,
the control unit of the extracorporeal blood treatment apparatus being configured for communicating with the control system of the blood warming device wherein the control system of the blood warming device is configured to:
receive said information defining said identified current operational mode, and
if the identified current operational mode of the apparatus is a mode wherein there is no blood flow through the extracorporeal blood circuit or a mode wherein the extracorporeal blood circuit is not connected to a patient cardiovascular system, then impose a switch off or a reduction of electric power at least to the heating components of the blood warming device.

25. The assembly according to claim 21, wherein the control system of the blood warming device is configured to:
receive said calculated value of the maximum threshold,
receive, from a power absorption sensor, a power information signal indicative of the electric power currently supplied to the heating components of the blood warming device,
compare said supplied electric power against said maximum threshold power, and
if it is detected that the supplied electric power is greater or equal to said maximum threshold, reduce the electrical power supplied to the heating components.

26. The apparatus according to claim 1, wherein the blood warming device is part of the extracorporeal blood treatment apparatus.

27. The apparatus according to claim 1, wherein the blood warming device is separate from the extracorporeal blood treatment apparatus.

28. An assembly including an extracorporeal blood treatment apparatus and a blood warming device,
wherein the extracorporeal blood treatment apparatus includes:
a holding portion configured for receiving an extracorporeal blood circuit having a treatment unit, a blood withdrawal line connected to a blood inlet of the treatment unit, and a blood return line connected to an outlet of the treatment unit;
a blood pump which, when the extracorporeal blood circuit is received by the holding portion, is configured for controlling the flow of blood flowing through at least one of said blood withdrawal line and blood return line;
at least one treatment fluid source;
at least one treatment fluid line in fluid communication with the at least one treatment fluid source and in direct or indirect fluid communication with said extracorporeal blood circuit to supply treatment fluid to the extracorporeal blood circuit; and
a control unit connectable with the blood warming device;
wherein the blood warming device includes a heating section provided with heating components, and which is configured for receiving and heating a corresponding portion of the extracorporeal blood circuit; and
wherein the control unit of the extracorporeal blood treatment apparatus is configured to:
establish a communication with said blood warming device;
identify, among a plurality of modes of operation of the apparatus, a current operational mode which the apparatus is performing;
calculate an electric power maximum threshold allowed to be supplied to the heating components of the blood-warming device, wherein the power maximum threshold is calculated based at least on measured or set flow rates of the treatment fluid from the at least one treatment fluid source in said at least one treatment fluid line, and
generate a control signal for the blood warming device based on the calculated electric power maximum threshold, the control signal including at least one of the following:
a command directed to impose to the blood warming device a mode of operation depending upon the identified current operational mode of said apparatus, or
information defining said identified current operational mode.

29. An extracorporeal blood treatment apparatus comprising:
a holding portion configured for receiving an extracorporeal blood circuit having a treatment unit, a blood withdrawal line connected to a blood inlet of the treatment unit, and a blood return line connected to an outlet of the treatment unit;
a blood pump configured to control the flow of blood flowing through at least one of said blood withdrawal line and blood return line when the extracorporeal blood circuit is received by the holding portion;

at least one treatment fluid source;

at least one treatment fluid line in fluid communication with the at least one treatment fluid source and in direct or indirect fluid communication with said extracorporeal blood circuit to supply treatment fluid to the extracorporeal blood circuit; and a control unit connectable with a blood warming device having heating components, the control unit configured to:
- establish a communication with said blood warming device,
- identify, among a plurality of modes of operation of the apparatus, a current operational mode which the apparatus is performing,
- calculate an electric power maximum threshold allowed to be supplied to the heating components of the blood-warming device, wherein the power maximum threshold is calculated based at least on measured or set flow rates of the treatment fluid from the at least one treatment fluid source in said at least one treatment fluid line, and
- generate a control signal for the blood warming device based on the calculated electric power maximum threshold, the control signal including at least one of the following:
  - a command directed to impose to the blood warming device a mode of operation depending upon the identified current operational mode of said apparatus, or
  - an information defining said identified current operational mode; and wherein the apparatus includes the extracorporeal blood circuit with the treatment unit having a semipermeable membrane dividing the same treatment unit into a blood or primary chamber and a dialysate or secondary chamber, and wherein said at least one treatment fluid line of the apparatus includes at least one of:
- a fresh dialysate line connected to a dialysate inlet of said dialysate or secondary chamber,
- a pre-infusion line connected to said blood withdrawal line downstream said blood pump,
- a post-infusion line connected to said blood return line, downstream said blood-warming device,
- a pre-blood pump infusion line connected to said blood withdrawal line upstream said blood pump, or
- a waste line connected to an outlet of said dialysate or secondary chamber, and wherein the maximum threshold is calculated based at least on one or more of the following flow rates:
- a dialysate flow rate which is a set or measured value of flow through said fresh dialysate line,
- a pre-infusion flow rate which is a set or measured value of flow through said pre-infusion line,
- a post-infusion flow rate which is a set or measured value of flow through said post-infusion line,
- a pre-blood pump infusion flow rate, which is a set or measured value of flow through said pre-blood pump infusion line, or
- an effluent flow rate which is a set or measured flow rate through an effluent line.

* * * * *